US012232767B2

(12) United States Patent
Mozloom, Jr. et al.

(10) Patent No.: US 12,232,767 B2
(45) Date of Patent: *Feb. 25, 2025

(54) CANNULA ASSEMBLY

(71) Applicant: Cilag GmbH International, Zug (CH)

(72) Inventors: Joseph Mozloom, Jr., Cincinnati, OH (US); Christopher Brock Stone, San Francisco, CA (US); Andrew S. Berkowitz, Redwood City, CA (US); Steven G. Hall, Montgomery, OH (US); Jeffrey P. Wiley, Milford, OH (US); Richard Patrick Chesnes, Cincinnati, OH (US); Jeffery T. Kirk, Liberty Township, OH (US); Aren Calder Hill, Mountain View, CA (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,688

(22) Filed: Jun. 20, 2023

(65) Prior Publication Data
US 2023/0329752 A1 Oct. 19, 2023

Related U.S. Application Data

(62) Division of application No. 17/222,977, filed on Apr. 5, 2021, now Pat. No. 11,944,347.

(60) Provisional application No. 63/008,652, filed on Apr. 10, 2020, provisional application No. 63/086,013, filed on Sep. 30, 2020.

(51) Int. Cl.
A61B 17/34 (2006.01)
A61B 17/00 (2006.01)

(52) U.S. Cl.
CPC ...... *A61B 17/3423* (2013.01); *A61B 17/3474* (2013.01); *A61B 2017/00367* (2013.01)

(58) Field of Classification Search
CPC ............ A61B 17/3423; A61B 17/3474; A61B 17/3421; A61B 17/3498; A61B 17/3496; A61B 2017/00367
See application file for complete search history.

(56) References Cited

U.S. PATENT DOCUMENTS

| 5,906,595 A | 5/1999 | Powell et al. |
| 7,963,975 B2 * | 6/2011 | Criscuolo .......... A61B 17/0218 606/190 |

(Continued)

FOREIGN PATENT DOCUMENTS

EP 2432408 B1 3/2016

OTHER PUBLICATIONS

International Search Report and Written Opinion for Application No. PCT/IB2021/052811, dated Jul. 8, 2021, 12 pages.

(Continued)

*Primary Examiner* — Tracy L Kamikawa
(74) *Attorney, Agent, or Firm* — Frost Brown Todd LLP

(57) ABSTRACT

In examples, a method of operating a surgical device comprises disengaging an obturator from a funnel portion of a cannula; removing a shaft portion of the obturator from a cannula lumen of the cannula; disengaging a seal cartridge from the funnel portion of the cannula; and removing the seal cartridge from the funnel portion after removing the shaft portion of the obturator from the cannula lumen.

19 Claims, 47 Drawing Sheets

(56) References Cited

U.S. PATENT DOCUMENTS

| | | | |
|---|---|---|---|
| 8,137,318 B2* | 3/2012 | Schweitzer | A61B 17/3462 |
| | | | 604/167.01 |
| 8,206,411 B2 | 6/2012 | Thompson et al. | |
| 8,795,223 B2 | 8/2014 | Stearns et al. | |
| 8,968,250 B2 | 3/2015 | McGinley et al. | |
| 9,498,107 B2 | 11/2016 | Doyle et al. | |
| 10,172,687 B2 | 1/2019 | Garbus et al. | |
| 2005/0077689 A1 | 4/2005 | Hueil | |
| 2008/0132847 A1 | 6/2008 | Wing et al. | |
| 2009/0118586 A1 | 5/2009 | Griffin | |
| 2011/0087159 A1 | 4/2011 | Parihar et al. | |
| 2013/0303851 A1 | 11/2013 | Griffith et al. | |
| 2014/0276465 A1 | 9/2014 | Lambrecht et al. | |
| 2015/0196322 A1 | 7/2015 | Sauter | |
| 2015/0351794 A1 | 12/2015 | Mastri et al. | |
| 2017/0095269 A1 | 4/2017 | Reid et al. | |
| 2018/0168688 A1 | 6/2018 | Schmid et al. | |
| 2018/0168746 A1 | 6/2018 | Swayze et al. | |
| 2018/0333144 A1* | 11/2018 | Rhad | A61B 90/17 |
| 2019/0000506 A1* | 1/2019 | Parihar | A61B 17/0469 |
| 2019/0090905 A1 | 3/2019 | Hall et al. | |
| 2019/0216497 A1* | 7/2019 | Doerr | A61B 17/3417 |
| 2020/0038059 A1 | 2/2020 | McGinley et al. | |
| 2020/0100815 A1 | 4/2020 | Reid et al. | |

OTHER PUBLICATIONS

International Preliminary Report on Patentability for Application No. PCT/IB2021/052811, dated Oct. 20, 2022, 9 pages.

Partial Supplementary European Search Report, European Patent Application No. 21785079.1, Mar. 20, 2024, 13 pages.

Japanese First Office Action dated Dec. 17, 2024, for Application No. 2022-561518, 5 pages.

* cited by examiner

CANNULA ASSEMBLY

CROSS-REFERENCE TO RELATED APPLICATIONS

This present application is a divisional of U.S. patent application Ser. No. 17/222,977, filed Apr. 5, 2021, now U.S. Pat. No. 11,944,347, issued on Apr. 2, 2024, which claims the benefit and priority of U.S. Provisional Patent Application No. 63/008,652, filed Apr. 10, 2020, and also claims the benefit and priority of U.S. Provisional Patent Application No. 63/086,013, filed Sep. 30, 2020, the entireties of each of these applications are incorporated herein by reference.

TECHNICAL FIELD

Systems and methods disclosed herein related to medical devices, and more particularly to cannula assemblies for medical procedures.

BACKGROUND

Minimally invasive procedures allow for access to a targeted site within a patient with minimal trauma to the patient. For example, laparoscopic surgery can allow for surgical access to a patient's cavity through a small incision on the patient's abdomen. A cannula can form a surgical corridor to allow tools to access the patient's cavity. In some procedures, the patient's cavity can be insufflated to allow for increased access to the patient cavity and reduced trauma to the patient.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
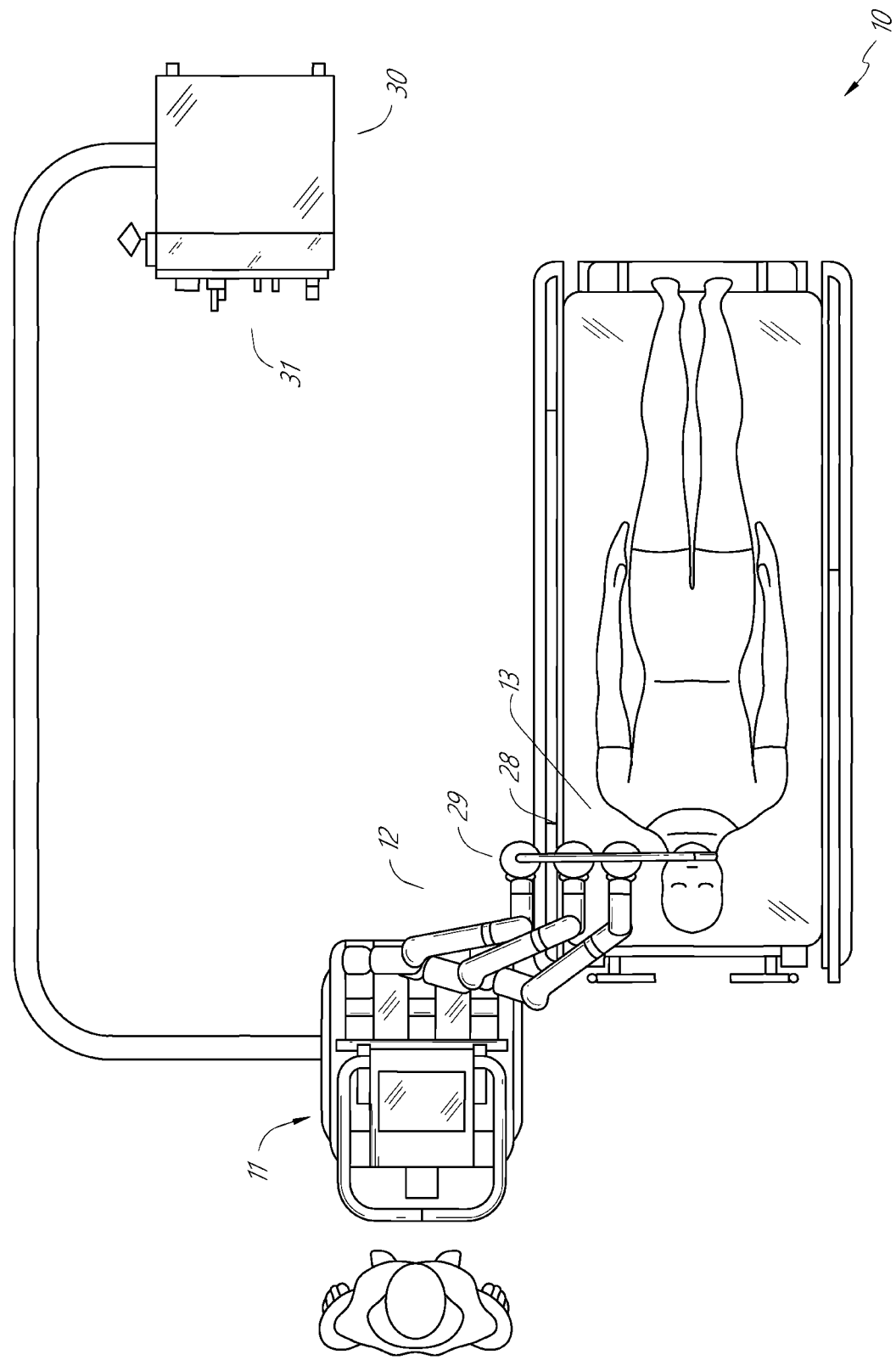
FIG. 1 illustrates an embodiment of a cart-based robotic system arranged for diagnostic and/or therapeutic bronchoscopy procedure(s).
Figure 2:
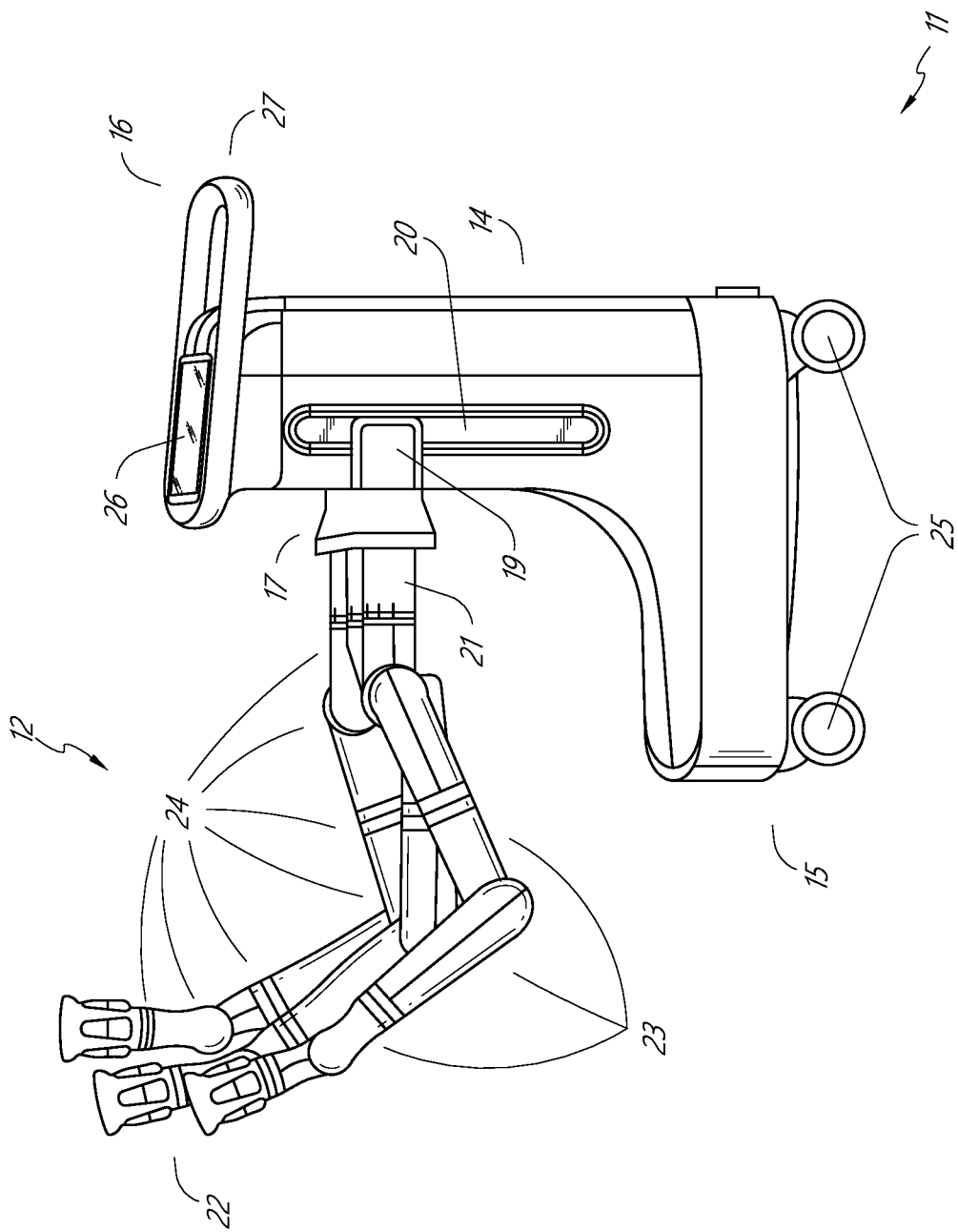
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
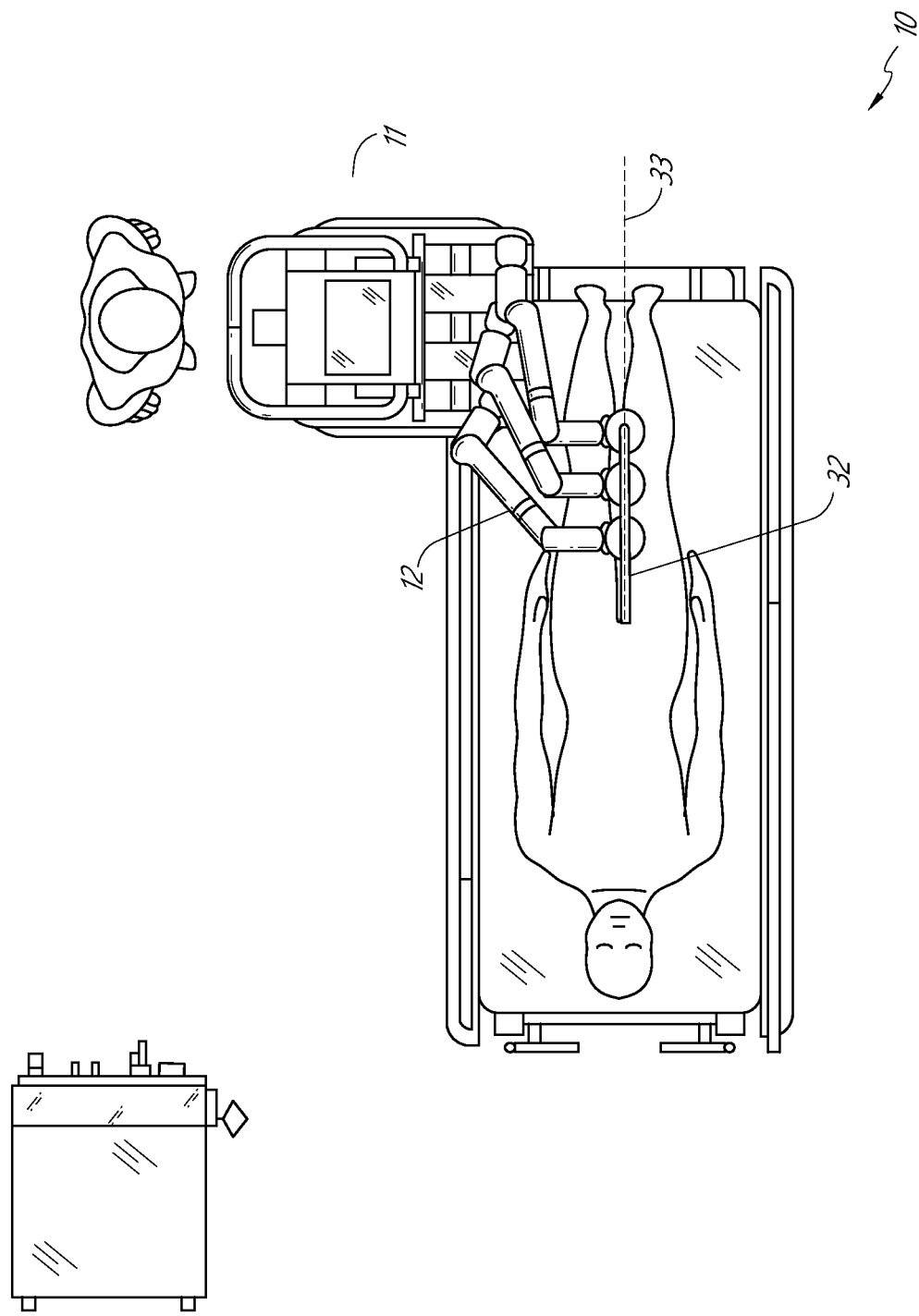
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
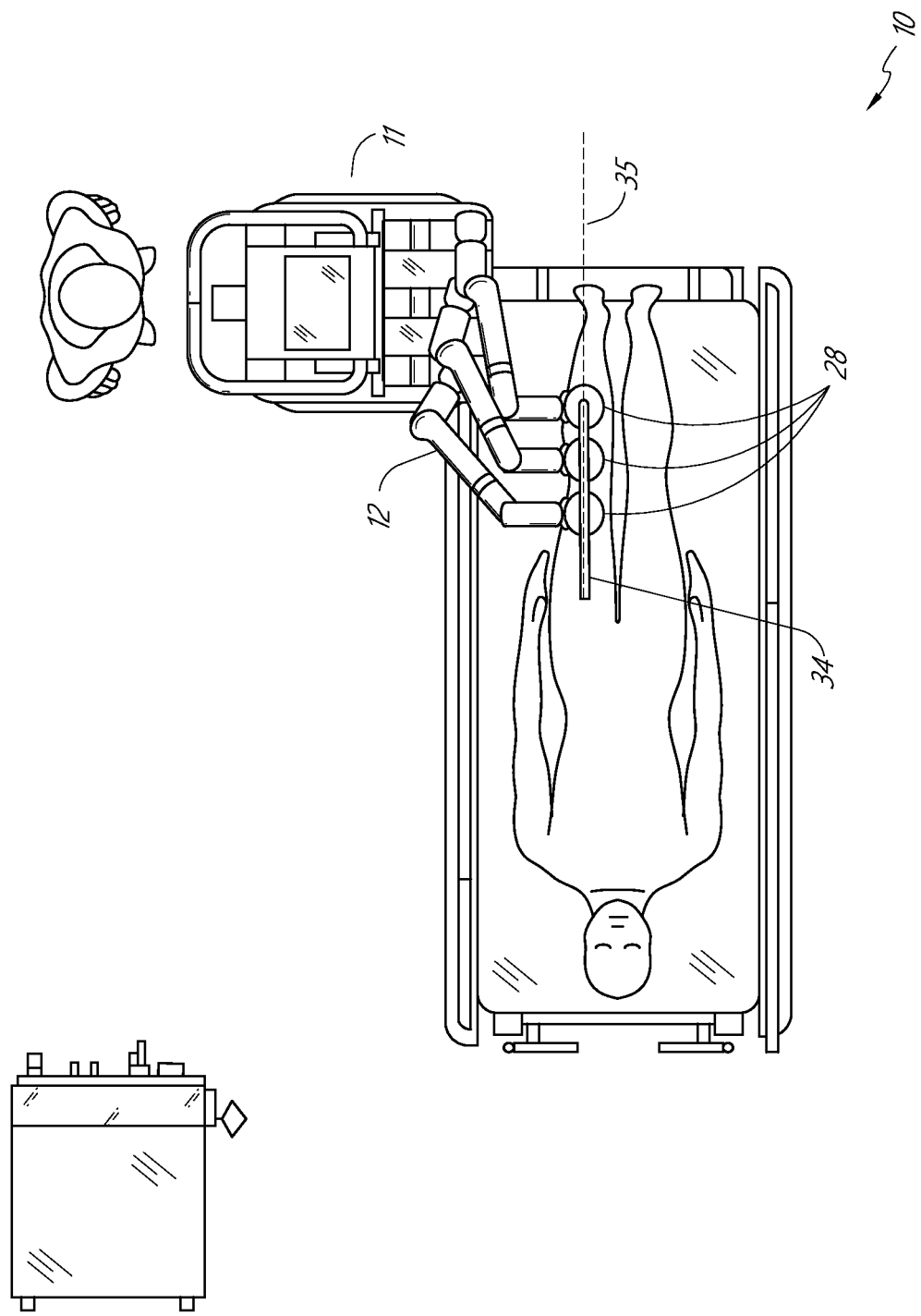
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
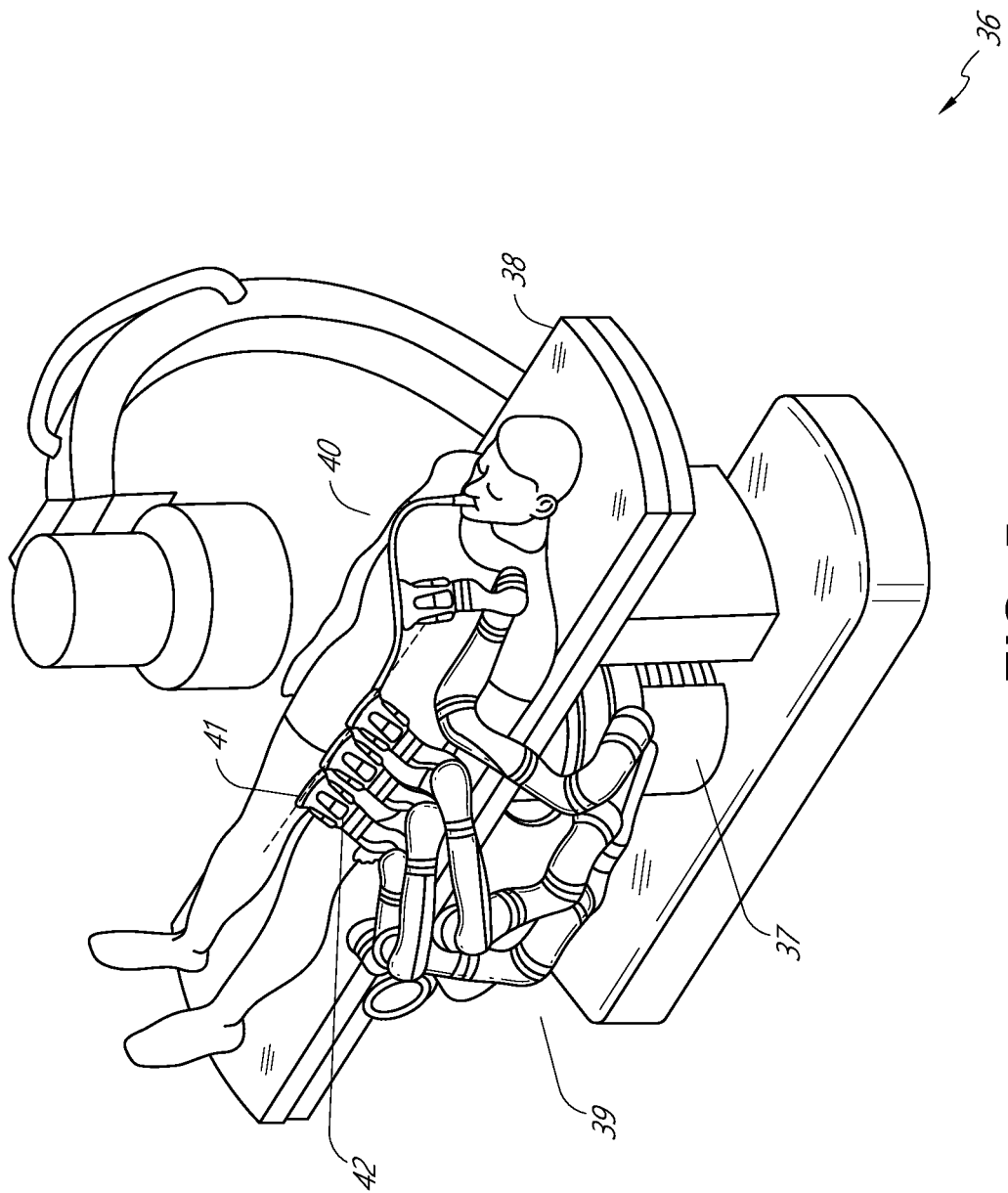
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
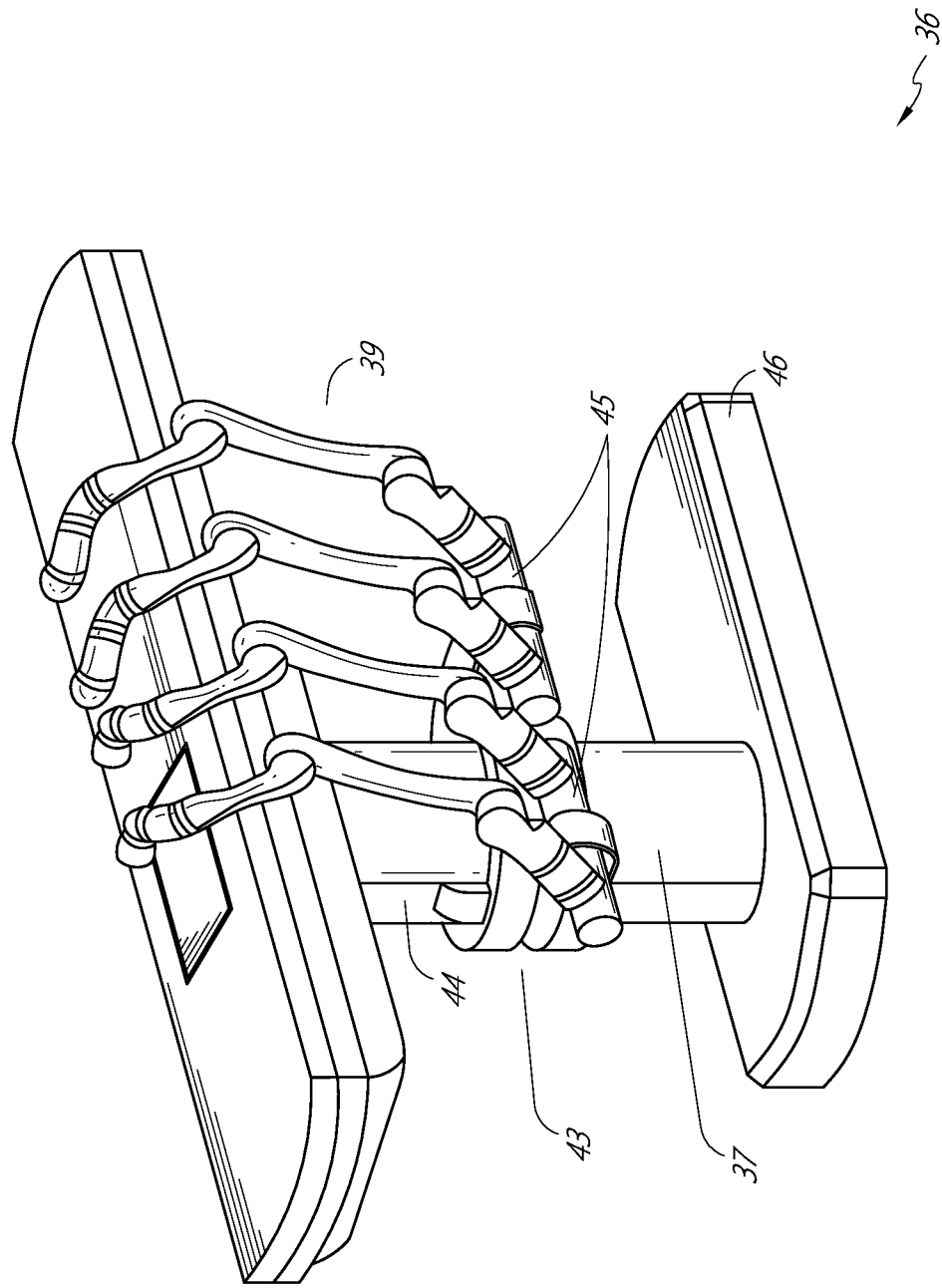
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
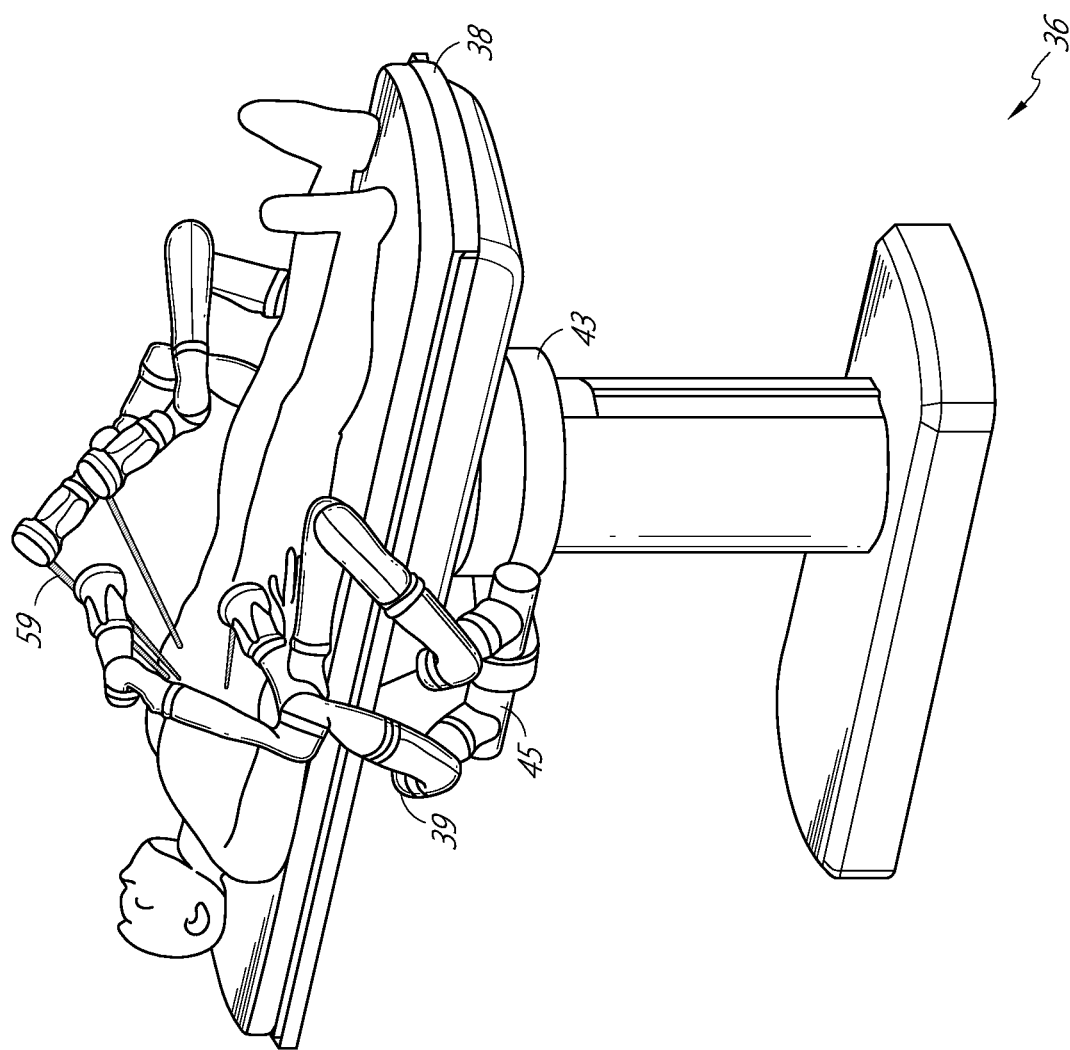
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
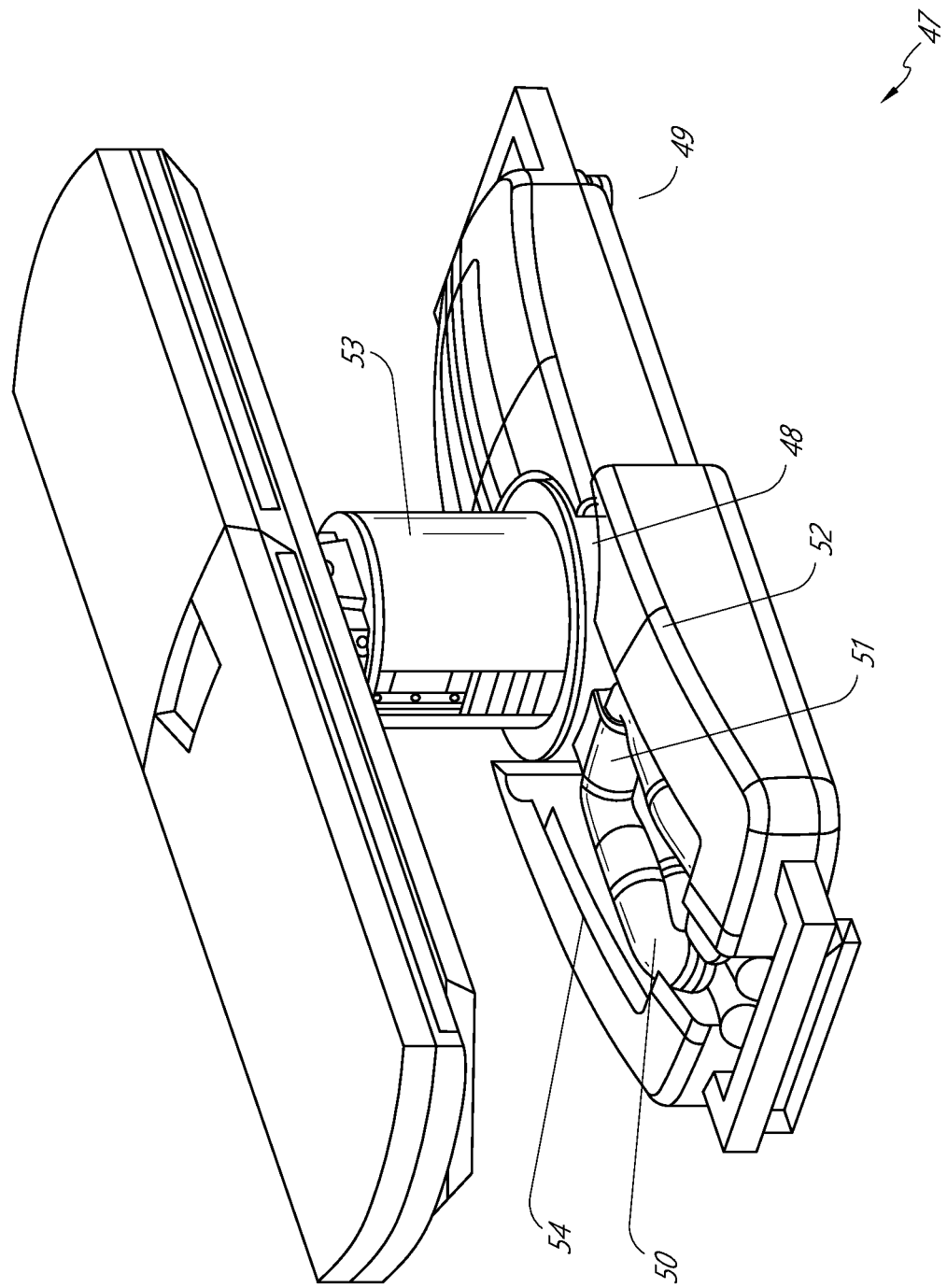
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
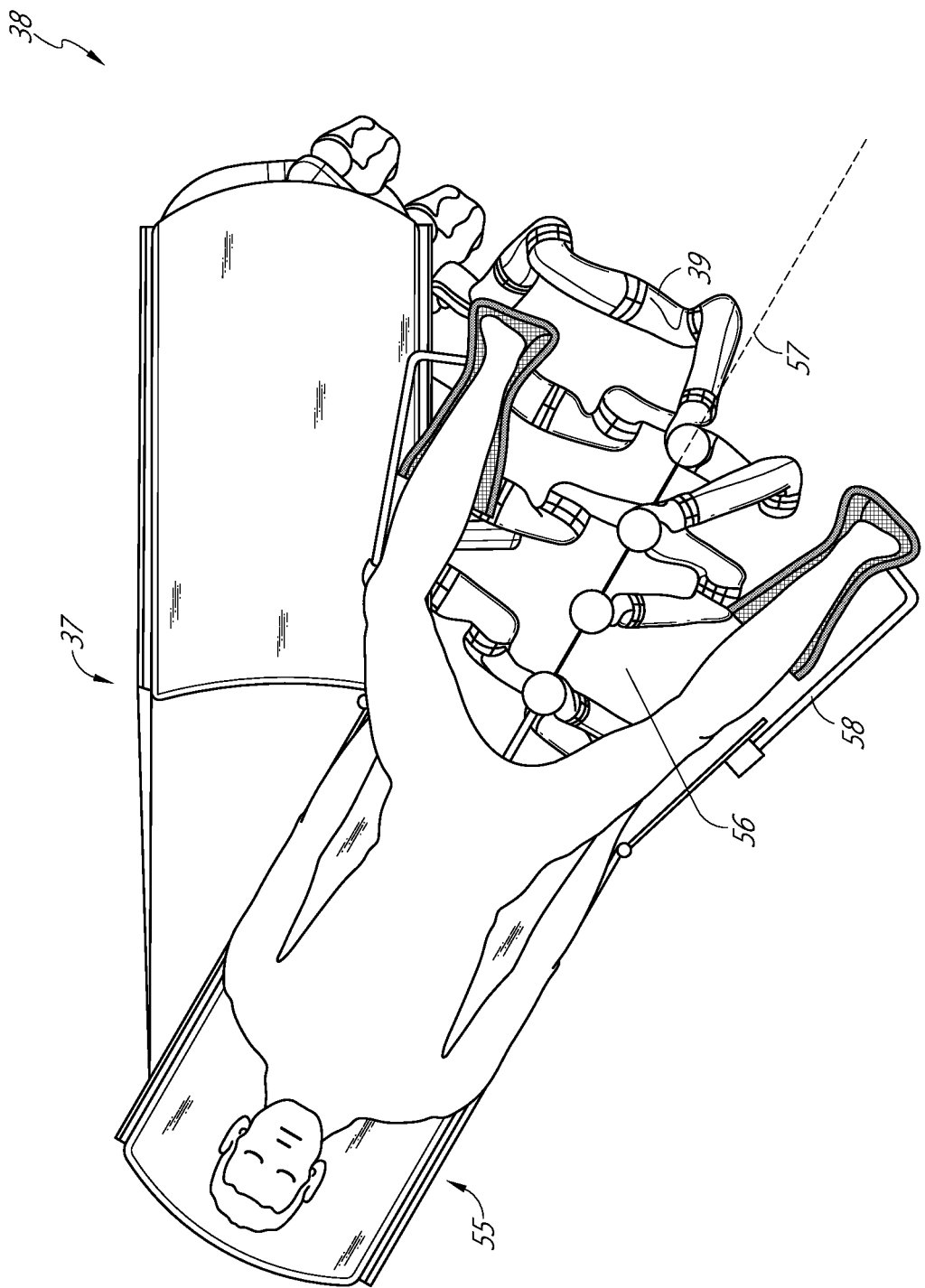
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
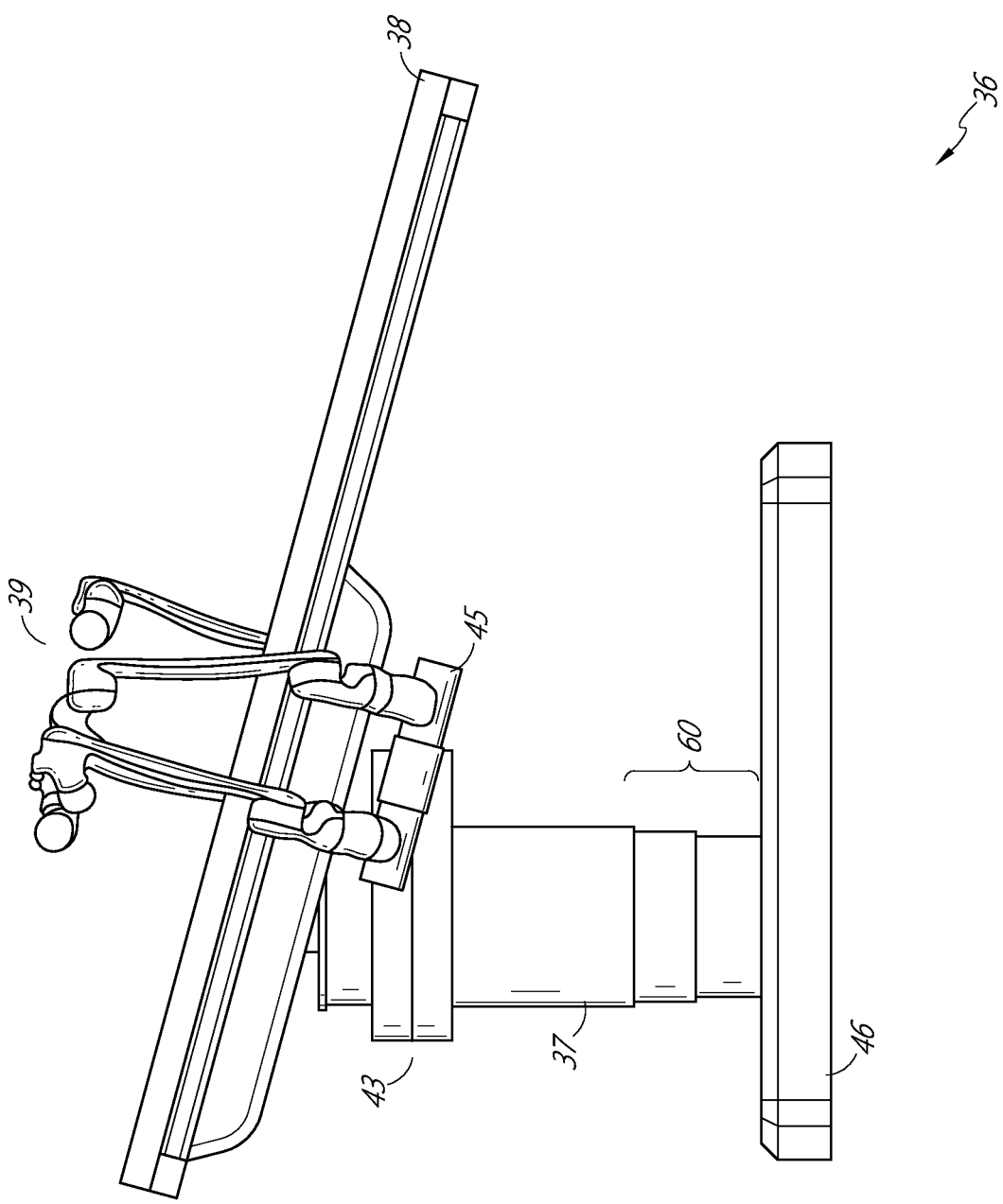
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
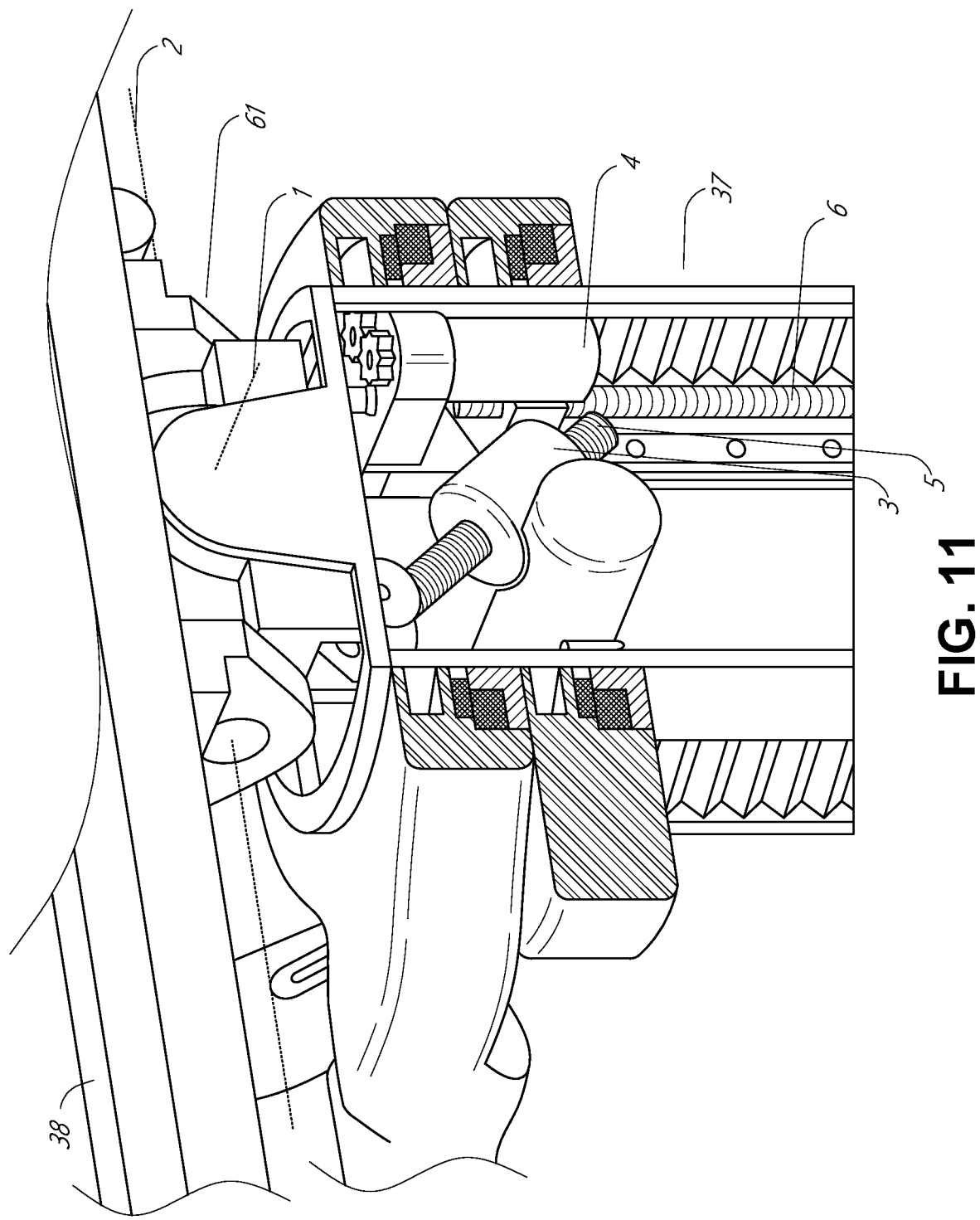
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
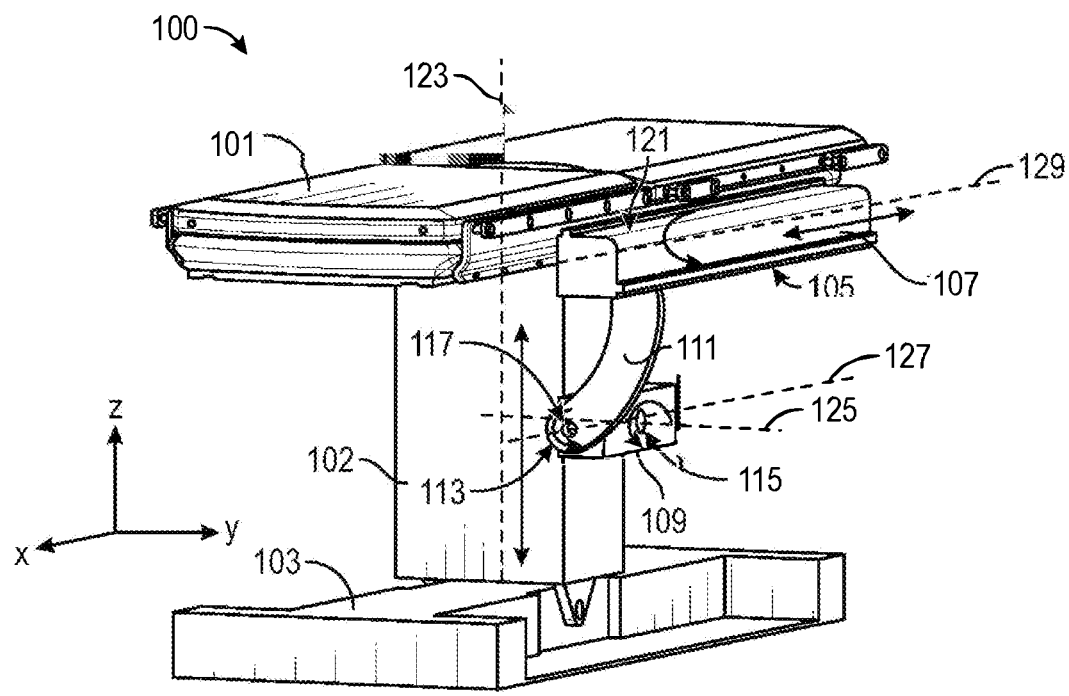
FIG. 12 illustrates an alternative embodiment of a table-based robotic system.
Figure 13:
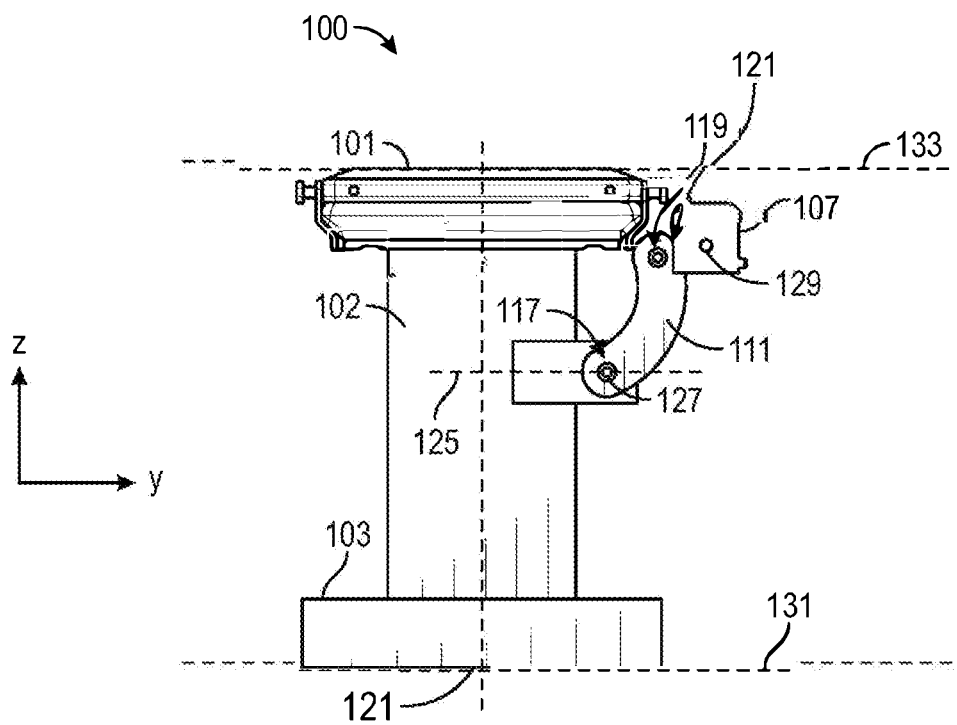
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
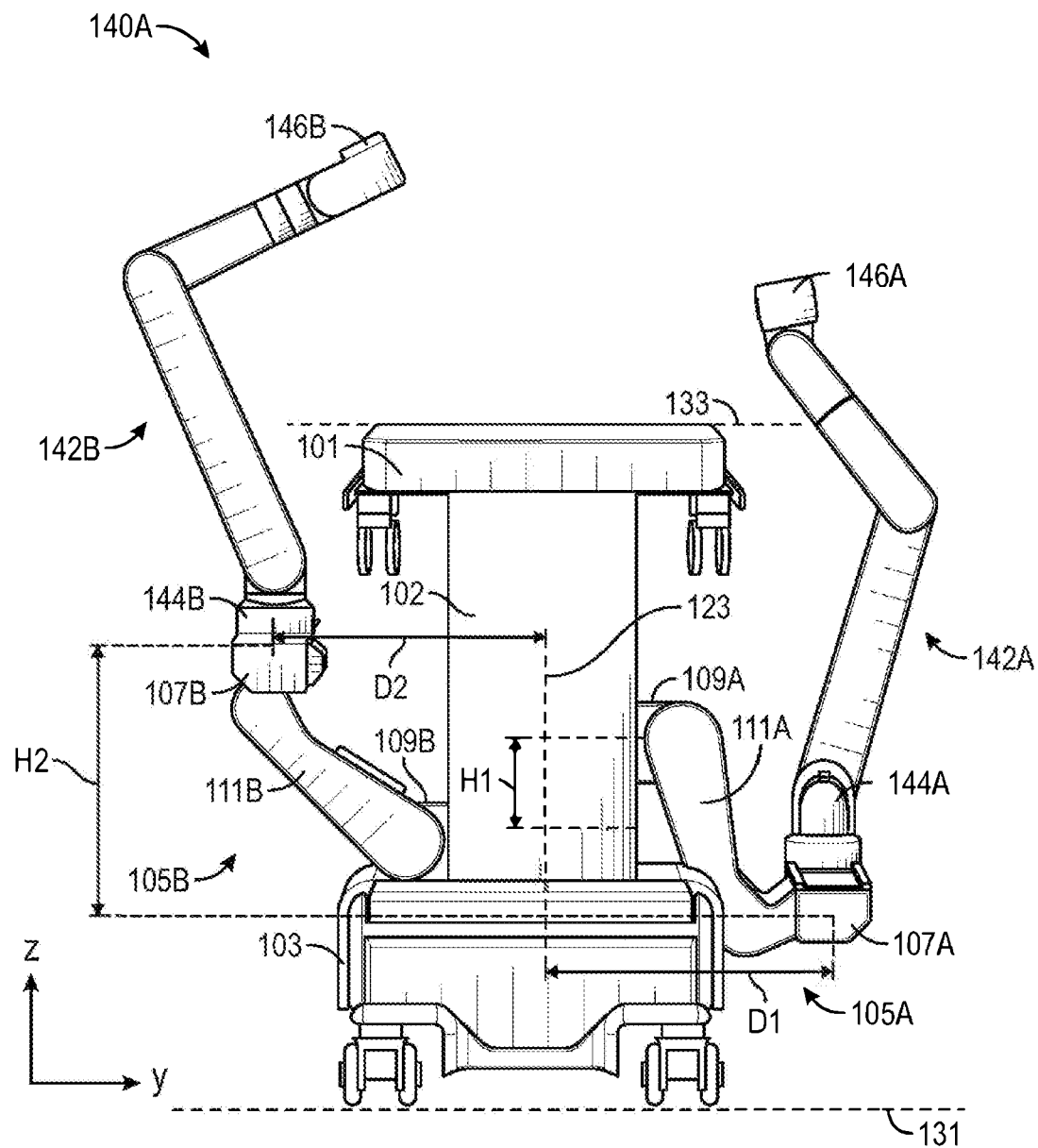
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (one degree of freedom, including insertion), a wrist (three degrees of freedom, including wrist pitch, yaw, and roll), an elbow (one degree of freedom, including elbow pitch), a shoulder (two degrees of freedom, including shoulder pitch and yaw), and base 144A, 144B (one degree of freedom, including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
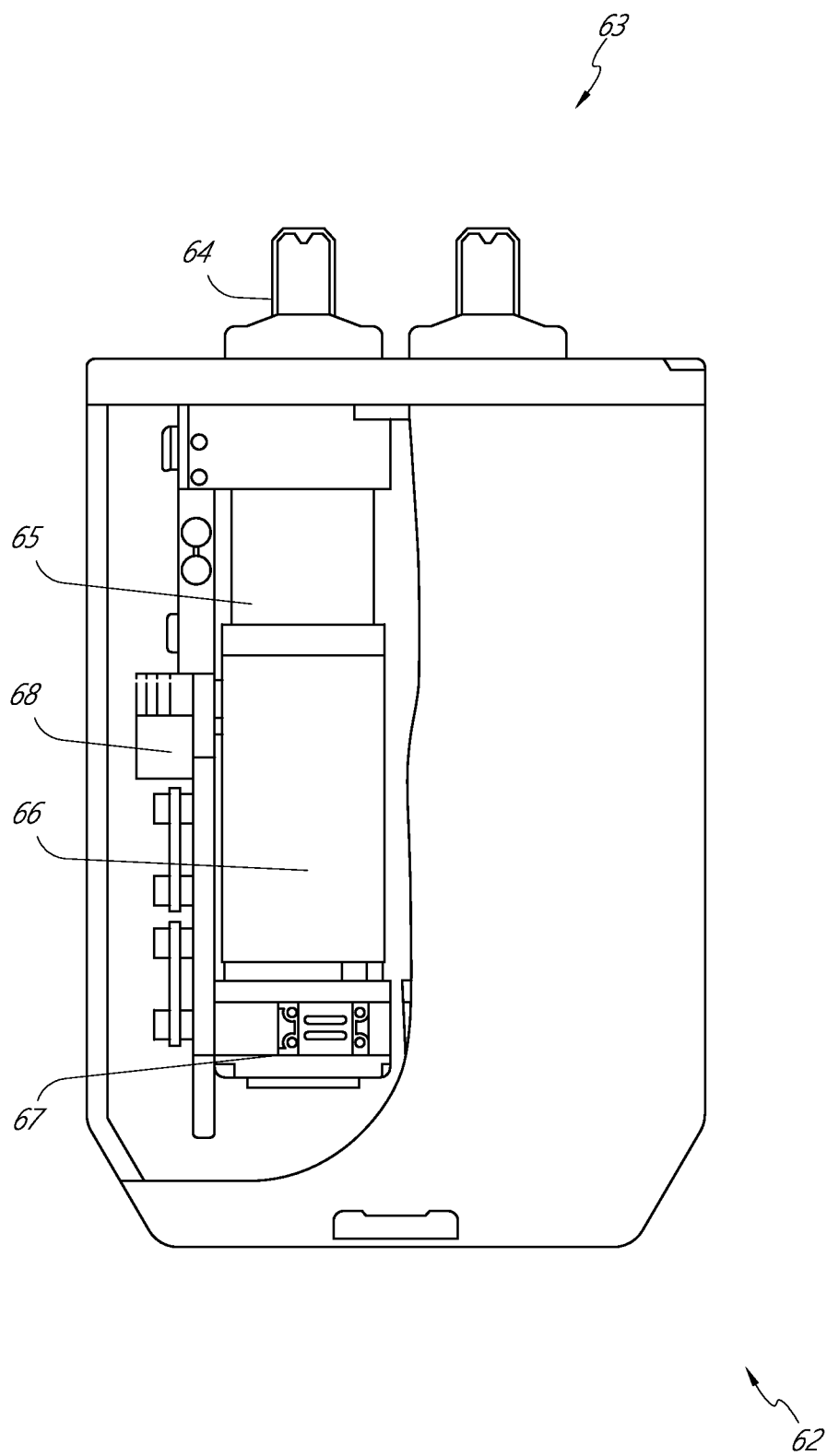
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
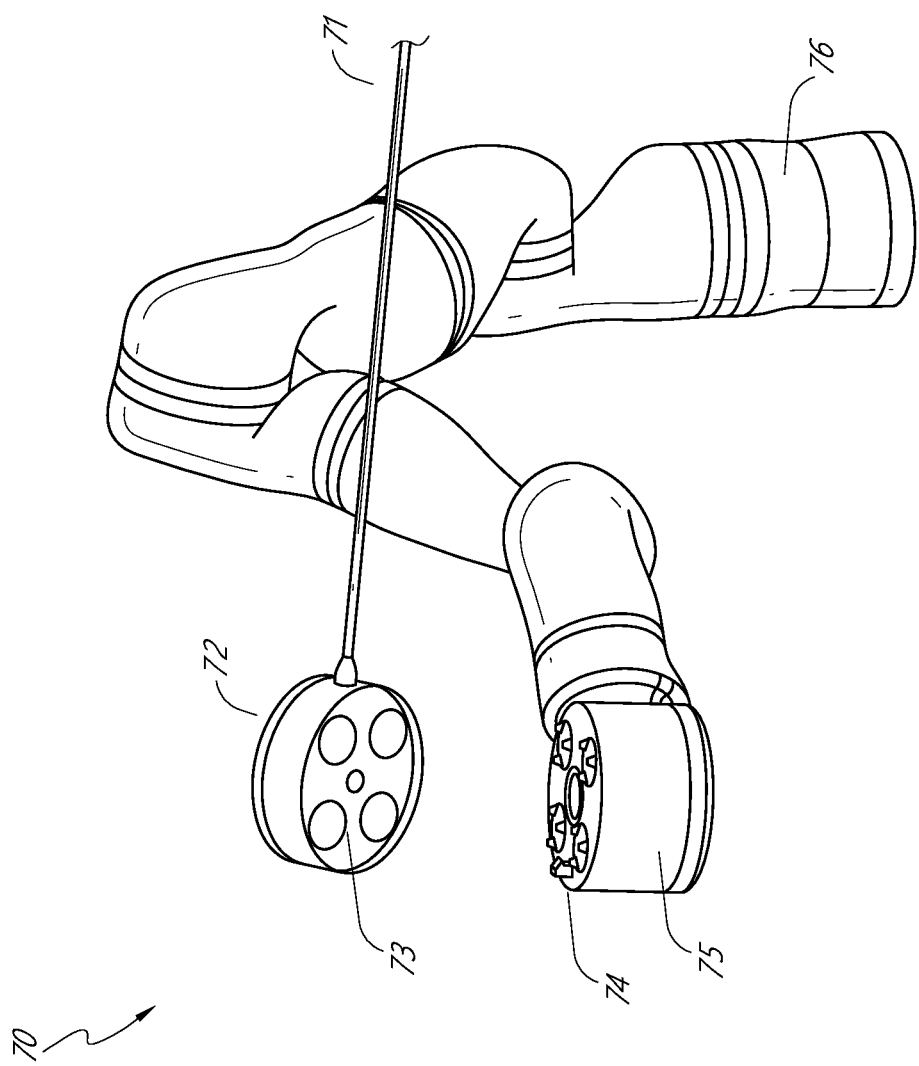
FIG. 16 illustrates an exemplary medical instrument with a paired instrument driver.

FIG. 16 illustrates an example medical instrument with a paired instrument driver Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
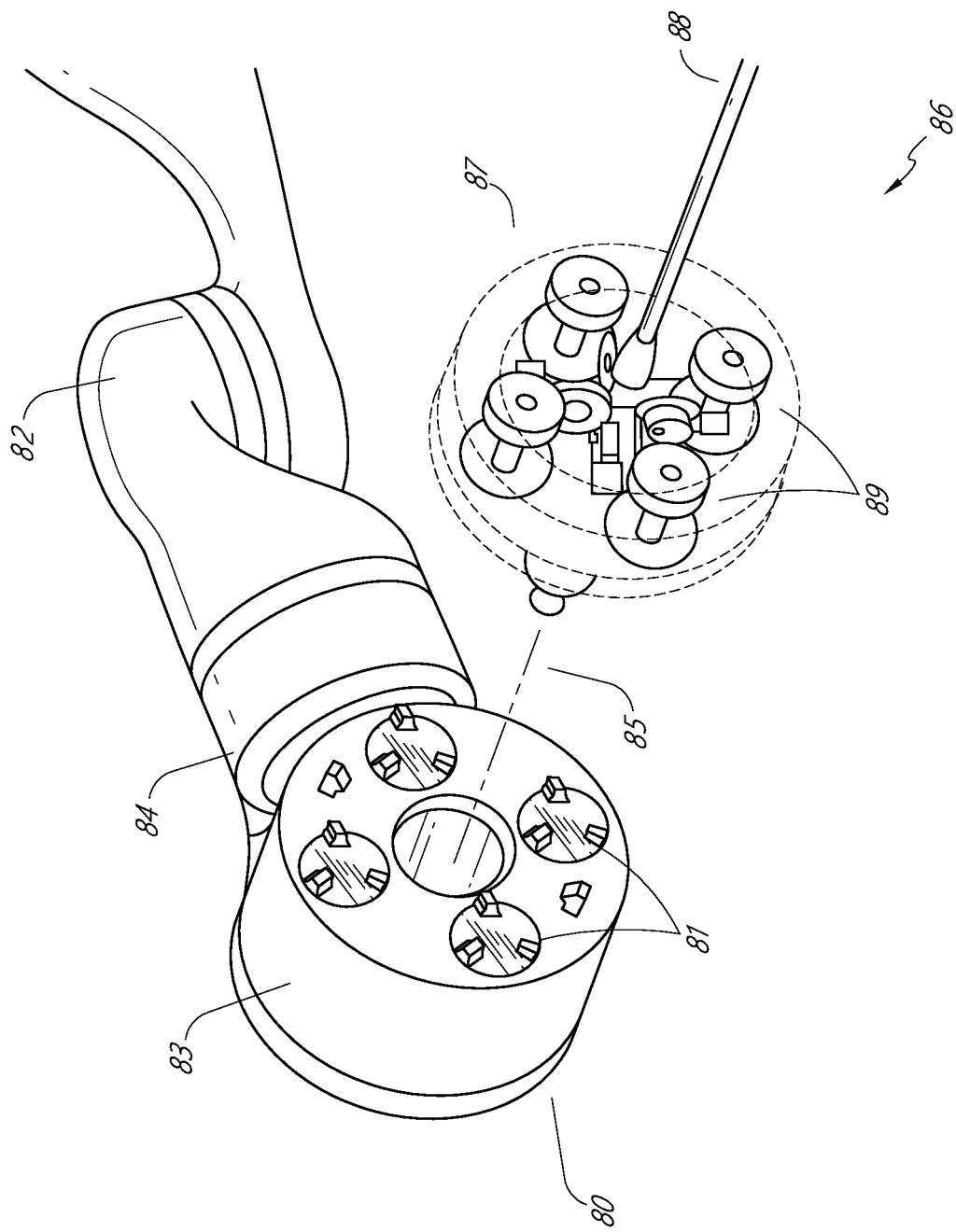
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
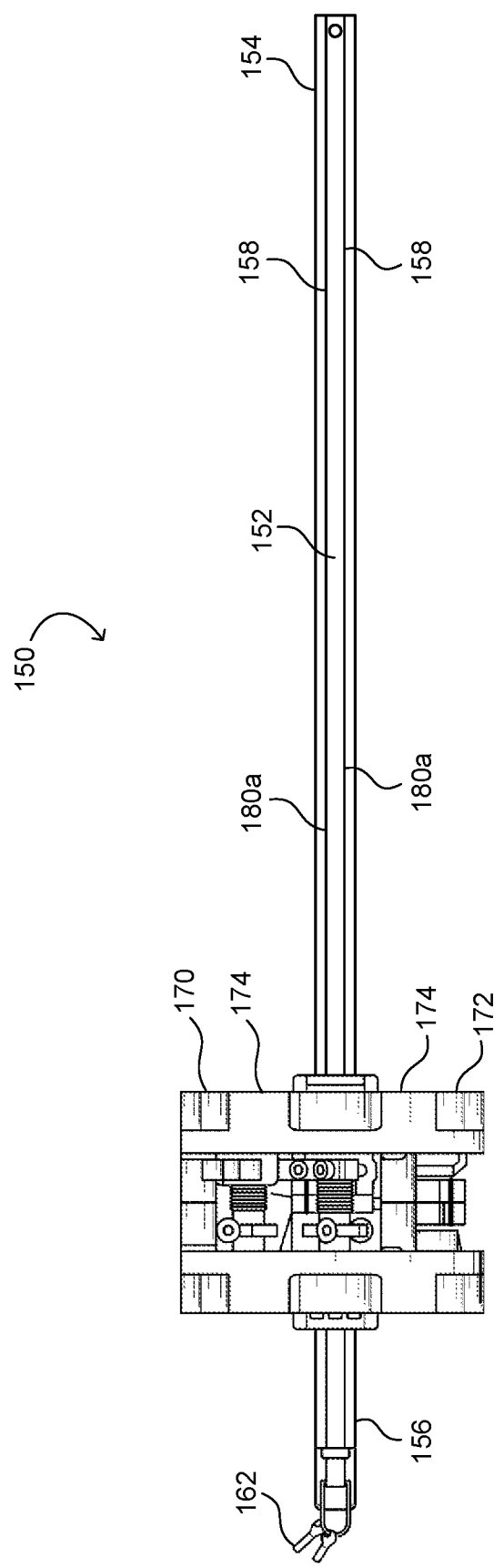
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
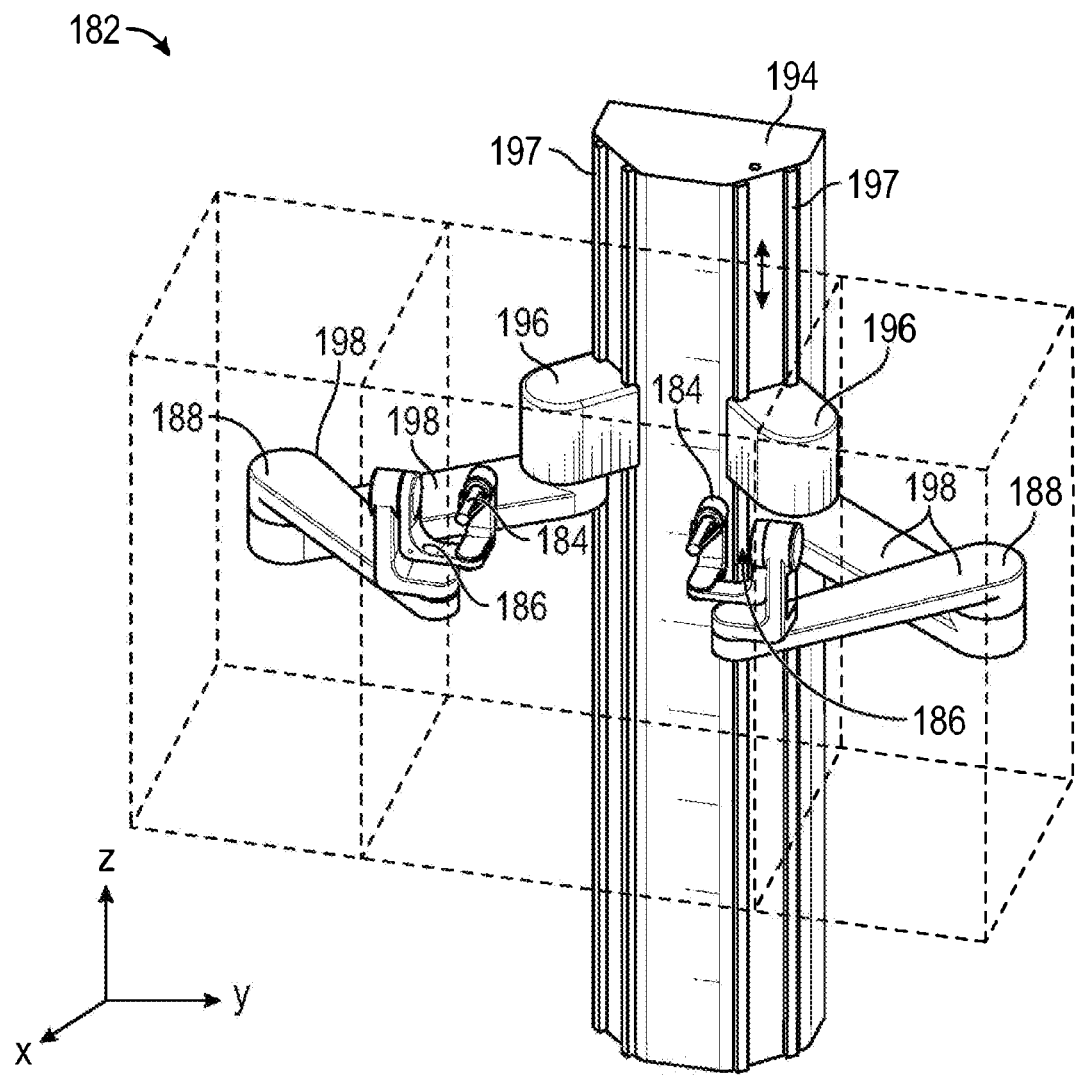
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
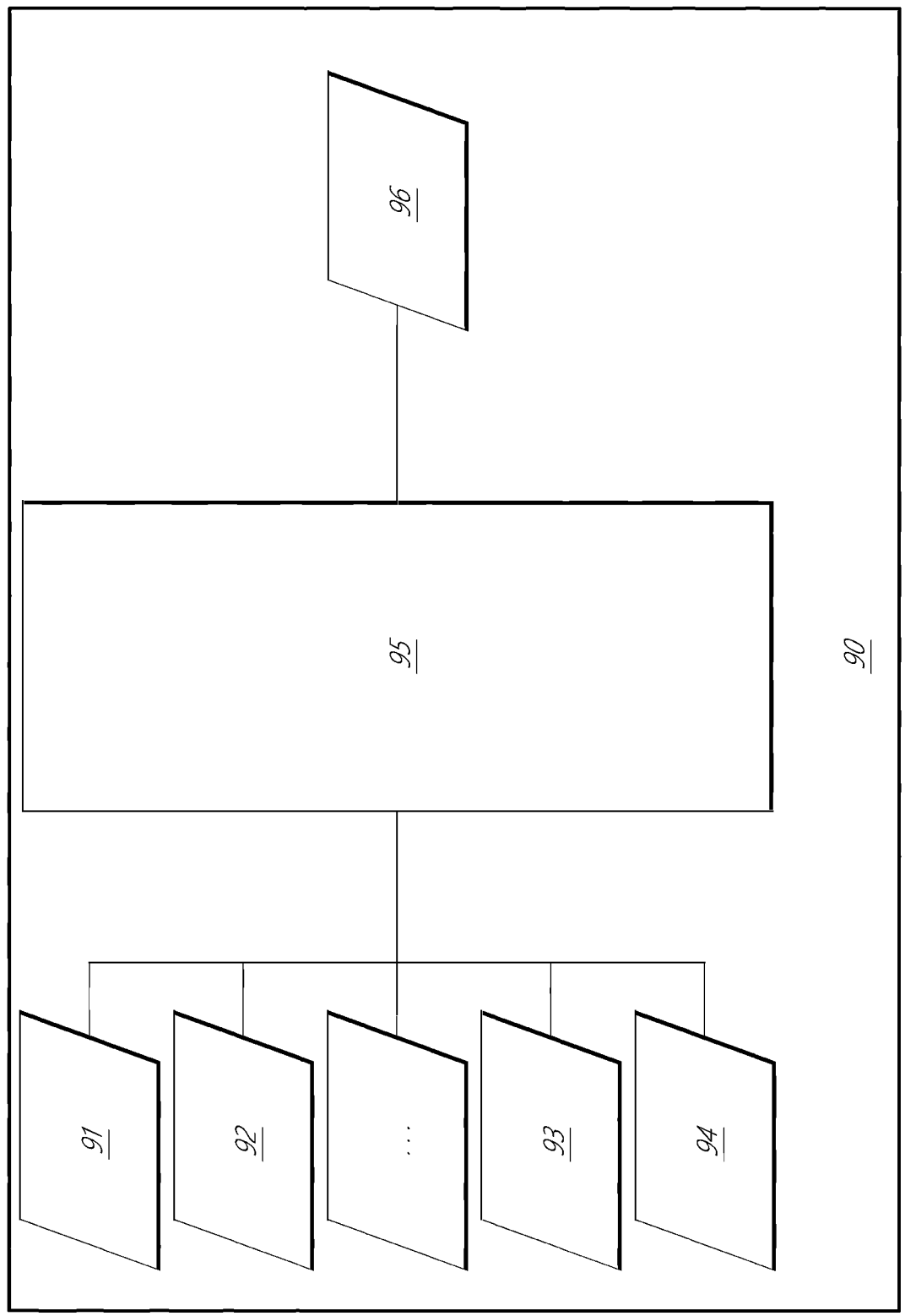
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, now U.S. Pat. No. 9,763,741, issued on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Trocar Assemblies

Embodiments of the disclosure include systems and techniques related to trocar assemblies and cannulas, such as, for example, trocar assemblies for laparoscopic procedures.

Assemblies disclosed herein can overcome one or more challenges discovered with respect to certain conventional trocar assemblies. In certain trocar assemblies, a clinician may have difficulty engaging and disengaging the seal cartridge from the cannula. Accordingly, during some procedures, a clinician may require additional time to insert or remove the seal cartridge or may not be able to fully engage the seal cartridge, which may compromise insufflation in the patient cavity. Further, in certain trocar assemblies, the seal cartridge is disposed within an upper portion of the cannula. Accordingly, the configuration of certain trocar assemblies may interfere with robust inline latching of the cannula to a robotic arm or detection of the cannula by a robotic system. Advantageously, the disclosed trocar assembly can allow for the seal cartridge to be easily engaged and disengaged from the cannula, while allowing for secure engagement for procedures. As can be appreciated, the configuration of the disclosed trocar assembly can reduce clinical errors, reduce procedure time, and simplify workflow.

Figure 21:
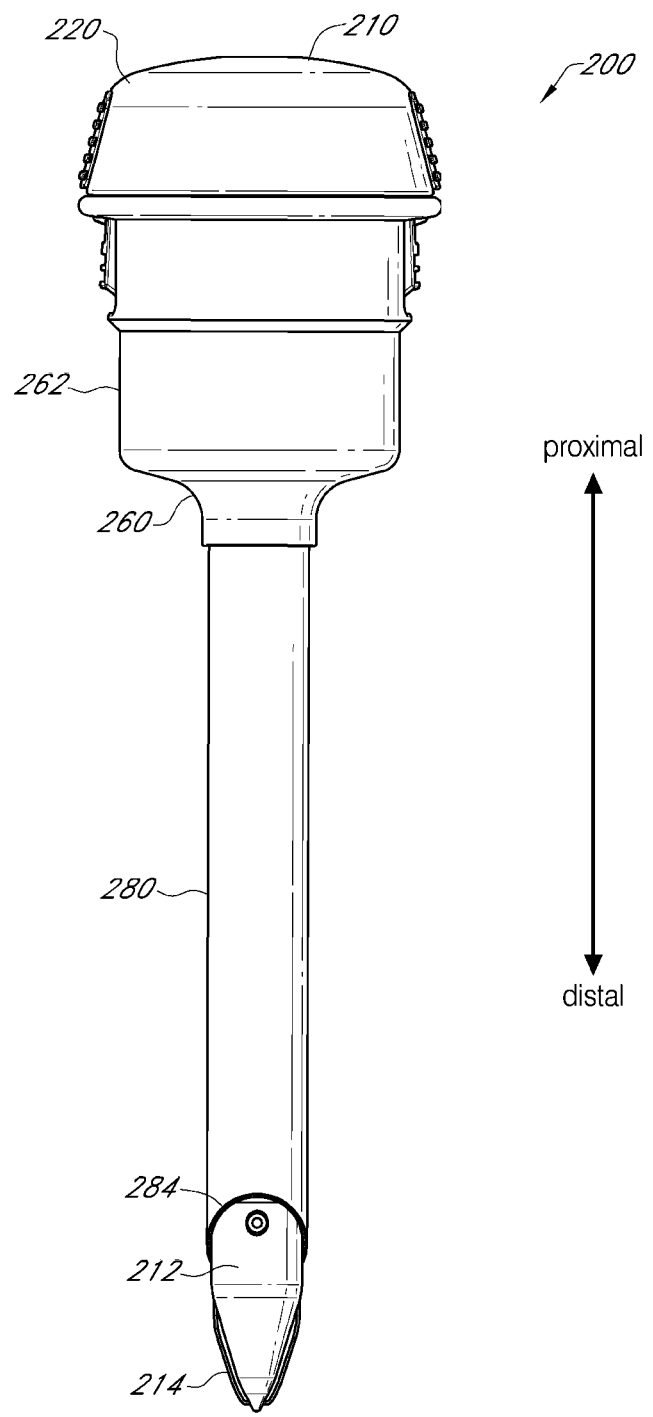
FIGS. 21 and 22 illustrate an exemplary trocar assembly.
Figure 22:
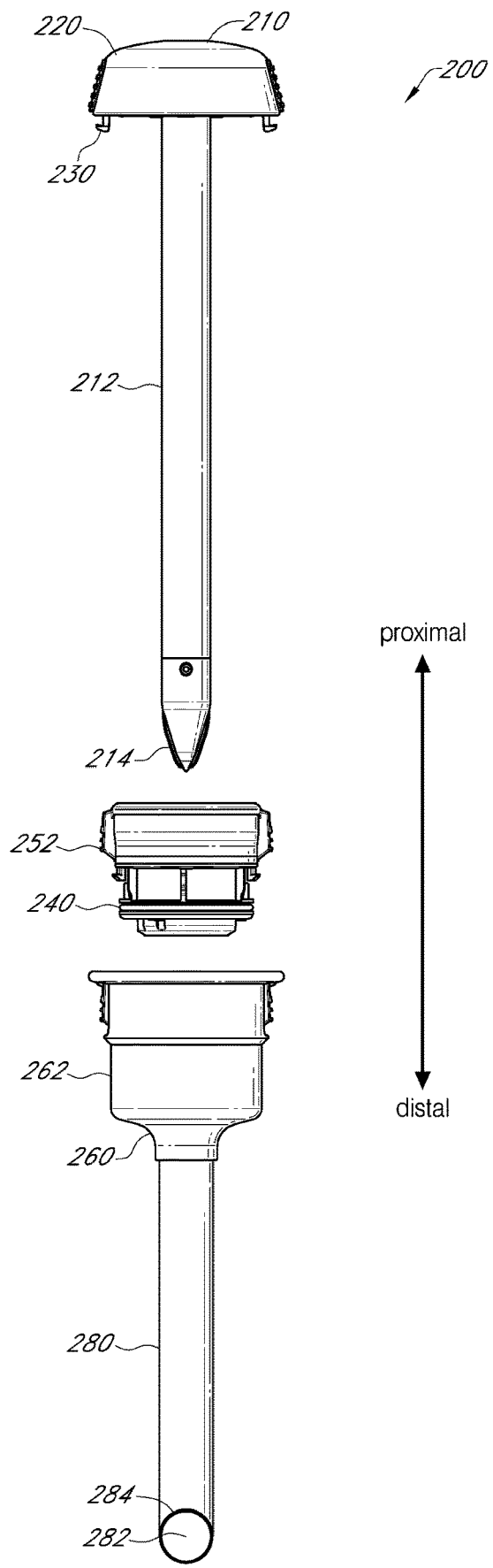

With reference to FIGS. 21-22, an exemplary trocar assembly 200 including an obturator 210, a seal cartridge 240, and a cannula 260 is shown. FIG. 21 illustrates a trocar assembly 200 in an assembled state. FIG. 22 illustrates an exploded view of the trocar assembly 200 of FIG. 23 in an unassembled state. In the depicted example, the trocar assembly 200 displaces or dissects soft tissue to allow the cannula 260 to be inserted into the patient cavity to provide access to a surgical site. According to some embodiments, the trocar assembly 200 is configured to provide access to a surgical site for laparoscopic procedures. Additionally or alternatively, the trocar assembly 200 can be configured to provide access to a site for urological, endoscopic, percutaneous, orthopedic, and/or or other medical or minimally invasive procedures in which a medical instrument is introduced to the site through the trocar assembly. In some applications, the trocar assembly 200 provides access to a surgical site for robotic laparoscopic procedures performed by robotic systems described herein. Additionally or alternatively, the trocar assembly 200 may be configured for use in manual laparoscopic procedures.

In the depicted example, the obturator 210 and the cannula 260 of the trocar assembly 200 can dissect or puncture soft tissue to permit the trocar assembly 200 to access the surgical site. As illustrated, a proximal portion of the cannula 260 is configured as a funnel portion 262 that permits tools, including obturator 210, to be inserted. Cannula shaft 280 is configured as a tubular portion that extends distally from the funnel portion and provides a lumen though which obturator shaft 212 extends. In the assembled configuration, an obturator shaft 212 extends through a cannula lumen 282 of the cannula shaft 280. The obturator shaft 212 can be longer than the cannula shaft 280 so that the obturator shaft extends past the distal end portion 284 of the cannula shaft 280.

The obturator shaft 212 can include a beveled or otherwise pointed distal end 214 that is configured to dissect or puncture soft tissue. During insertion, the distal end 214 of the obturator shaft 212 can displace soft tissue to allow the cannula shaft 280 to be inserted into the patient cavity. The obturator 210 can be advanced by a clinician applying force or otherwise manipulating the proximal portion 220 of the obturator 210. Optionally, the proximal portion 220 can be utilized by clinicians or other users as a handle to apply force or otherwise advance the obturator 210 and/or the trocar assembly 200 generally. As illustrated, the proximal portion 220 of the obturator 210 can have a generally larger radius than the shaft 212 to allow a user to easily apply more force to the shaft 212. Further, the proximal portion 220 can include a grasping portion or a planar surface to allow the clinician to advance the obturator 210.

As illustrated, the obturator 210 and the cannula 260 of the trocar assembly 200 can be coupled together to cooperatively dissect or puncture soft tissue to permit the trocar assembly 200 to access the surgical site. Therefore, in the assembled configuration, the cannula 260 can be advanced together with the obturator 210. As can be appreciated, the distal end portion 284 of the cannula shaft 280 can further displace soft tissue to allow the cannula shaft 280 to be inserted into the patient cavity.

Upon insertion of the trocar assembly 200 into the patient cavity, the obturator 210 can be removed from the cannula 260. After removing the obturator 210 from the cannula 260, the cannula lumen 282 can provide a working corridor or working channel through which other tools such as laparoscopic tools, surgical instruments, and/or scopes can be inserted, manipulated, and/or removed. Optionally, the movement of the cannula 260 and the tools can be manipulated or controlled by robotic systems described herein.

Optionally, a latching mechanism 230 of the obturator 210 can allow the obturator 210 to be coupled or released from the cannula 260. In some embodiments, the latching mechanism 230 can extend from the proximal portion 220 of the obturator 210 to releasably engage with other portions of the trocar assembly 200.

In some applications, the trocar assembly 200 can allow for insufflation of the patient cavity during procedures to provide access within the patient cavity while minimizing trauma to the patient. The seal cartridge 240 can maintain insufflation within the patient cavity after the introduction of gas into the patient cavity. The seal cartridge 240 can, for example, be configured as a removable sub-assembly or seal pack that provides a hermetic seal with the cannula 260. The seal cartridge 240 can be coupled to the cannula 260 to sealingly isolate the cannula lumen 282 from the environment to maintain insufflation within the patient cavity. During operation, the seal cartridge 240 can maintain isolation of the patient cavity while permitting tools, such as the obturator 210 to pass through a passage of the seal cartridge 240. Further, the seal cartridge 240 can sealingly engage against the cannula funnel 262 to maintain insufflation of the patient cavity. As illustrated, the seal cartridge 240 can be disposed at the proximal portion of the cannula 260. For example, the seal cartridge 240 can be disposed at least partially within the funnel portion 262 of the cannula.

In some applications, the seal cartridge 240 can be removed from the cannula 260. Optionally, the seal cartridge 240 and the cannula 260 may have differing useful lives facilitated by the removable engagement of the seal cartridge 240 with respect to the cannula 260. For example, the seal cartridge 240 can be configured as a single use disposable device (e.g., made from plastic) while the cannula 260 can be configured to be sterilized and re-used (e.g., made from metal). As described herein, a latching mechanism 252 of the seal cartridge 240 can allow the seal cartridge 240 to be coupled or released from the cannula 260. In some embodiments, the latching mechanism 252 can releasably engage with other portions of the trocar assembly 200.

According to some embodiments, the cannula 260 can be configured for use in a robotically enabled procedure. As described, the cannula 260 and seal cartridge 240 assembled therewith can be docked to a robotic manipulator. For example, the cannula 260 can be latched or otherwise attached to a robotic arm and/or instrument driver to couple the cannula 260 to the robot after removal of the obturator 210. Docking the cannula 260 to the robot can facilitate robotic manipulation of surgical tools through the cannula.

Figure 23:
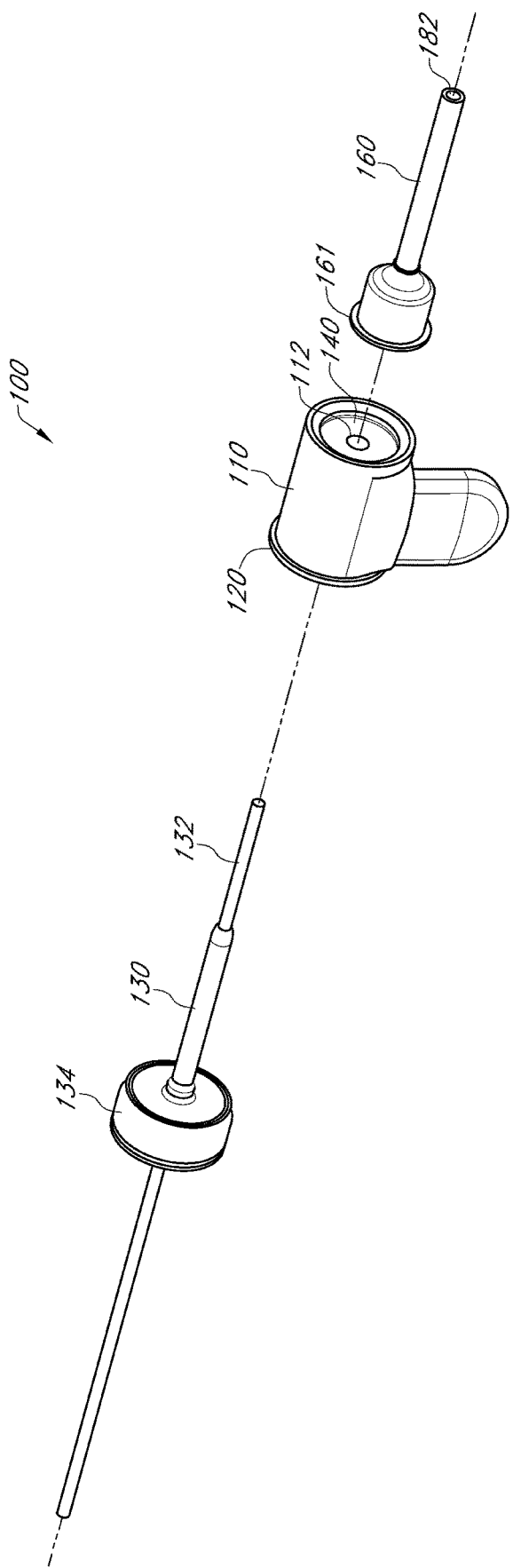
FIG. 23 illustrates an exemplary cannula docking arrangement in the robotics system.

FIG. 23 illustrates an exemplary cannula docking arrangement in the robotics system 100. The arrangement shown in FIG. 23 utilizes a compact instrument driver architecture in which the robotic driver is coupled to the cannula inline from the proximal end of the cannula.

As illustrated, the instrument driver 110 can have an accessory or cannula attachment interface 140 at a first side of the instrument driver 110 that is configured to attach to the cannula 160. An opposite side of the instrument driver 110 can have an instrument attachment interface 120 configured to couple to a medical instrument 130. A passage 112 extends through the instrument driver 110 to permit insertion or retraction of the instrument shaft 132 through the passage 112. The passage 112 can, for example, be configured as a lumen extending through the instrument driver 110 that has a greater diameter than the outer diameter of the instrument shaft 132. The passage 112 permits the instrument shaft 132 to extended or retracted through the passage 112.

According to some embodiments, the instrument driver 110 can be configured to operate mechanisms in the instrument 130 to insert or retract the instrument shaft 132 through the passage 112. For example, one or more drive outputs at the instrument attachment interface 120 of the instrument driver 110 can operate one or more inputs on the instrument base 134 of the instrument 130. Such inputs can be coupled to pull wires, gears, screws, and/or other mechanisms to convert rotary motion of the inputs to translational motion of the instrument shaft 132, thereby driving axial translation of the instrument shaft through the instrument driver 110.

As described herein, the cannula 160 can be configured as an access port that provides access to a patient cavity for the medical procedures, such as laparoscopic procedures. To facilitate insertion of the instrument 130 through the cannula, a proximal 161 of the cannula 160 can be attached to the instrument driver 110 with the axis or working channel 192 of the cannula 160 aligned with the passage 112 of the instrument driver 110. The cannula attachment interface 140 can retain the cannula 160 with a latching mechanism that engages the cannula 160 directly or through a sterile barrier, such as a sterile drape and/or sterile adapter.

Before insertion of the tool or instrument into the patient, the cannula 160 can be inserted and/or positioned within the patient cavity. The robotic arm can be moved or positioned to allow the instrument driver 110 and robotic arm to be docked and attached to the cannula 160. After docking to the cannula 160, the cannula attachment interface 140 of the robotic arm can retain the cannula 160 with the robotic arm or instrument driver 110. In some embodiments, the instrument driver 110 is configured to detect the cannula in order to facilitate docking, determine presence, and/or identify the cannula using any suitable sensing arrangement.

Figure 24:
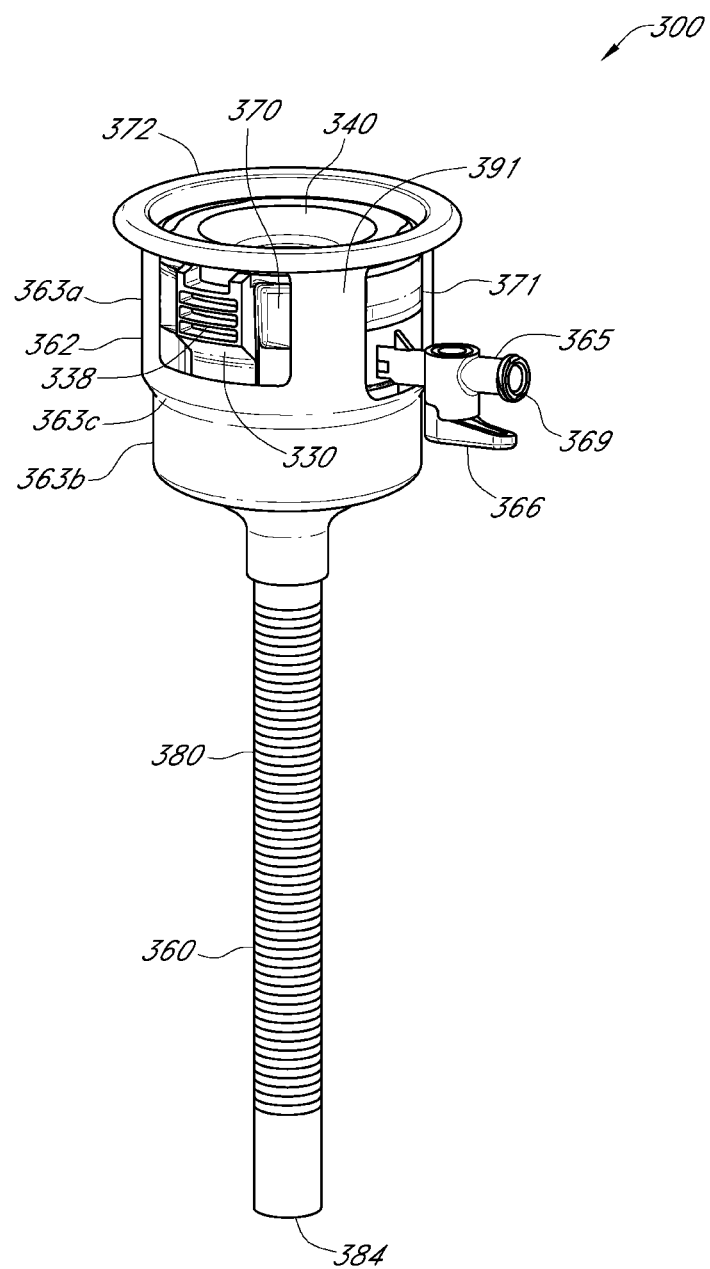
FIG. 24 illustrates an exemplary cannula assembly.
Figure 25A:
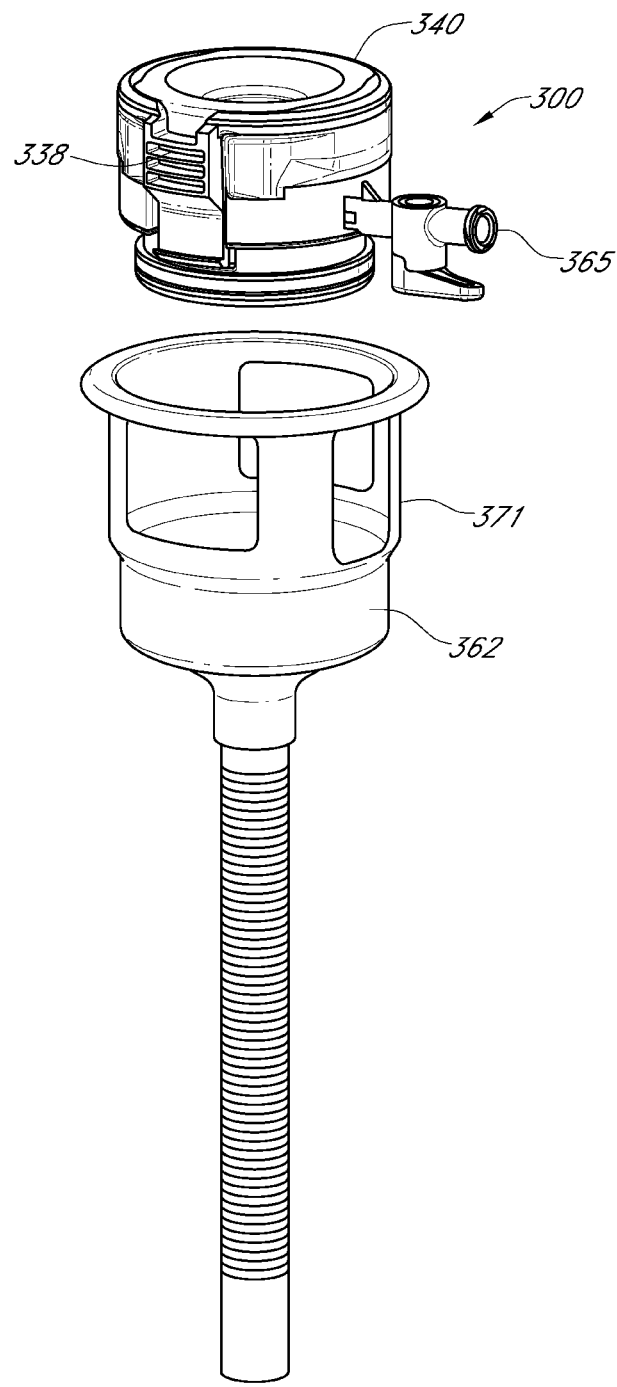
FIGS. 25A-25D illustrates the cannula assembly of FIG. 24 during various states of assembly.
Figure 25B:
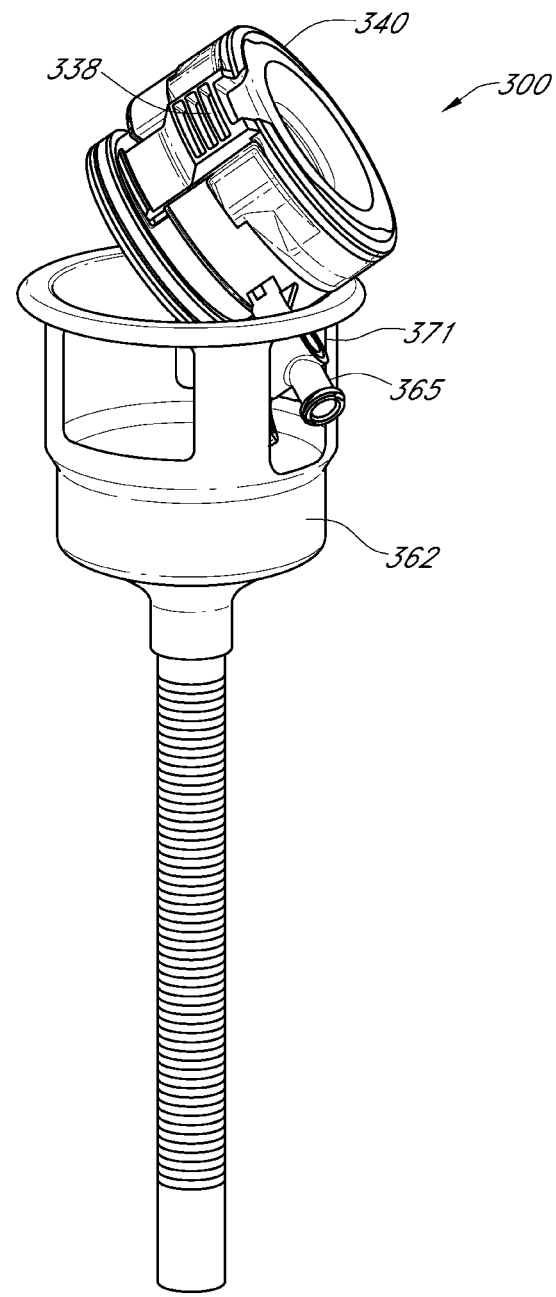
Figure 25C:
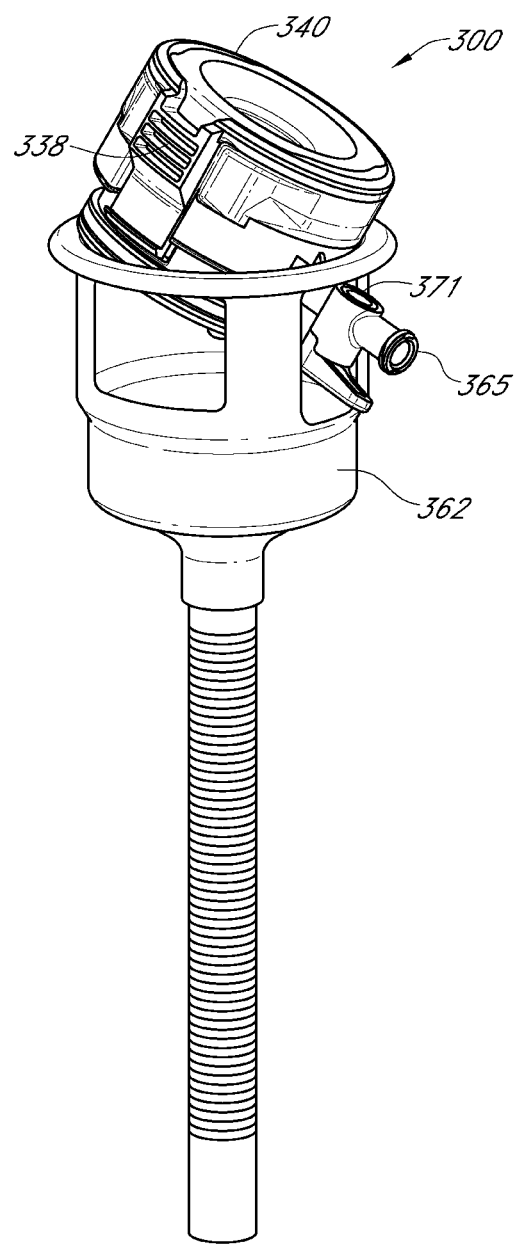
Figure 25D:
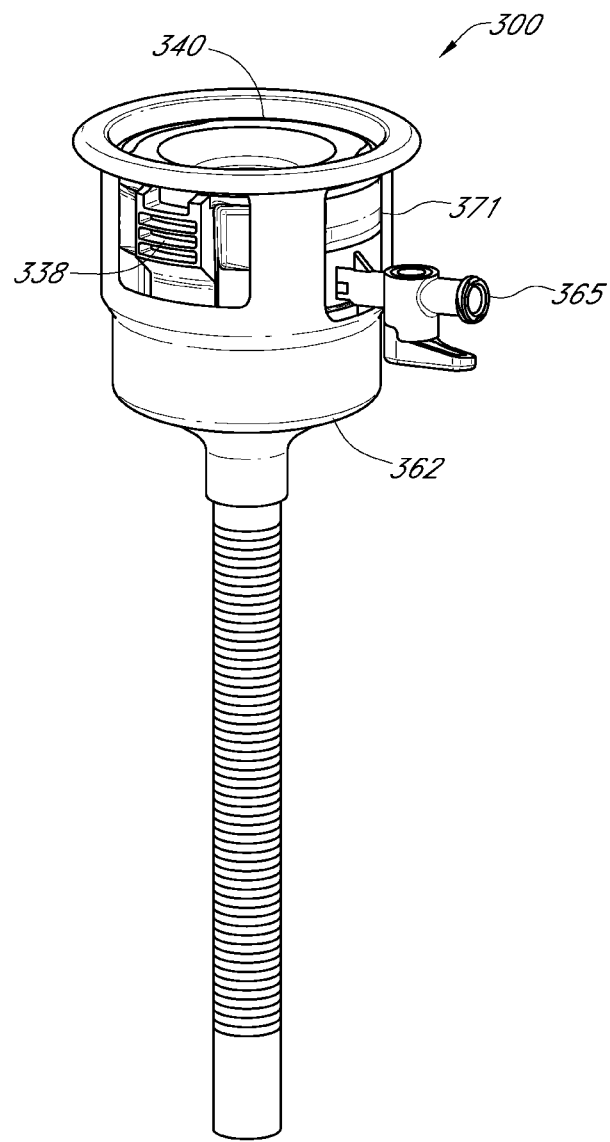

FIG. 24 illustrates a cannula assembly 300 including a cannula 360 and seal cartridge 340 with obturator removed. The cannula assembly 300 can be utilized with a trocar assembly 200 as described with respect to FIGS. 21-22 and/or the robotic docking arrangement shown in FIG. 23. Cannula 360 includes features that can facilitate removable attachment of the seal cartridge 340 to the cannula 360 without interfering with robotic capabilities of the assembly. The cannula assembly 300 can, for example, avoid interference of the seal cartridge 340 with a cannula latch on the instrument driver that securely engages the cannula 360 in a mechanically robust fashion. Alternatively, or in combination, the seal cartridge 340 can avoid obstructing a cannula detection sensor or distancing the proximal end of the cannula from a sensor that may be employed in the instrument driver. Alternatively, or in combination, the cannula assembly can facilitate attachment and/or removal of the seal cartridge in a user friendly fashion.

With reference to FIG. 24, upon insertion, the cannula 360 provides access to the patient cavity. As illustrated, the cannula 360 includes a shaft 380 extending from an upper portion or funnel 362 of the cannula 360. The shaft 380 defines a shaft lumen therein that provides access between the end portion 384 and the cannula funnel 362. As described herein, the end portion 384 of the shaft 380 can be advanced into the patient cavity to allow access to the patient cavity via the funnel 362.

During surgical procedures, the shaft lumen permits tools to access the patient cavity. The shaft lumen can have a generally circular inner cross-sectional profile to allow tools to be rotated within the shaft lumen. The shaft lumen can have an inner diameter suitable to permit tools to pass therethrough. The shaft 380 can also have a generally circular outer cross-sectional profile to allow the cannula 360 to rotate relative to the patient cavity.

The funnel portion 362 has an enlarged inner diameter that leads to a narrower inner diameter defined by the lumen of the cannula shaft 380. The enlarged geometry facilitates insertion of tools and/or the seal cartridge into the proximal portion of the cannula 360. For example, during the insertion of tools, such as the obturator 210 and/or instrument 130, the geometry of the funnel 362 can direct the tool shaft into the shaft lumen. In some embodiments, the funnel 362 can include a stepped geometry. As illustrated, the funnel 362 can include an upper funnel portion 363a and a lower funnel portion 363b. The lower funnel portion 363b can have a reduced diameter relative to the upper funnel portion 363a. Optionally, the funnel 362 can include a transition portion 363c between the upper tapered portion 363a and the lower tapered portion 363b.

The seal cartridge 340 can be coupled to the cannula 360 via the funnel portion 362. The geometry of the funnel 362 can permit devices such as the seal cartridge 340 to be disposed within the funnel 362 of the cannula 360. For example, as seen in FIG. 24, the seal cartridge 340 can be seated within the funnel portion 362 of the cannula 360 such that the seal cartridge does not protrude substantially beyond the proximal end of the cannula 360.

As illustrated in FIG. 24, the funnel walls of the funnel 362 can extend beyond the seal cartridge 340 when the seal cartridge 340 is seated within the funnel 362 to allow the seal cartridge 340 to be recessed within the funnel 362. As can be appreciated, by recessing the seal cartridge 340 within the cannula 360, the seal cartridge 340 can permit the proximal end of the cannula 360 to securely attach and dock with other components, such as the obturator 210 and/or the robotic arm. Although shown in a recessed arrangement, it is also contemplated that the proximal end of the seal cartridge 340 can be substantially flush with the proximal end of the cannula 360 when in an assembled or coupled configuration. Further, it is also contemplated that certain principles of this disclosure may be applied to embodiments in which the seal cartridge 340 protrudes proximally beyond the proximal end of the cannula funnel portion 362 when assembled with the cannula 360.

Fluids, such as gas for insufflation, can be introduced into the patient cavity via a fluid port 365 of the cannula assembly 300. Some examples of gases that may be introduced through the fluid port 365 to distend an abdominal cavity via insufflation include carbon dioxide and air. Alternatively, or in combination, the fluid port 365 can be configured to introduce or transfer other fluids, such as saline, liquids, or other fluidic media for irrigation, distension of orthopedic joints, or distension of other patient cavities. In some embodiments, a fluid port can be formed in the cannula. In the depicted example, the fluid port 365 is formed in the seal cartridge 340. As illustrated, the fluid port 365 is attached to the body of the seal cartridge and extends from the body of the seal cartridge 340. In some embodiments, the fluid port 365 extends radially from the body of the seal cartridge 340. The fluid port 365 can be in fluid communication with the cannula lumen when the seal cartridge and the cannula are coupled together in an assembled configuration. Fluid port 365 can be configured as a valve, such as a stop cock, that allows flow through the port to be opened, closed, or otherwise controlled. In the depicted example, fluid port 365 includes a lever 366 that can be manually controlled by a user to open and close the port. Fluid port 365 is also illustrated with a connector interface 369, such as a luer fitting, that allows insufflation lines or other fluid conduits to be connected or removed from the cannula assembly 300 as desired.

The funnel 362 can include features to allow the seal cartridge 340 to be retained or otherwise coupled to the funnel 362. As illustrated, seal cartridge 340 includes a latch mechanism 330 that can engage features of the funnel portion 362 to secure the seal cartridge 340 to the cannula 360. Latch mechanism 330 includes one or more release buttons 338 that can be operated to release the latch mechanism 330 and disengage the seal cartridge from the cannula 360.

Cannula 360 includes features along the sidewall 391 that permit access to portions of the seal cartridge through the sidewall. In some applications, the engagement or latching mechanism of the seal cartridge 340 can be accessible through one or more windows or voids 370 formed through the funnel wall. For example, void 370 can be configured as a latch window that permits a user to actuate a release button 338 through the sidewall 391. In some embodiments, the funnel 362 can include two opposing latching windows 370 disposed radially across from each other to permit access to two opposing release buttons 338 of the seal cartridge 340. As illustrated, the latching windows 370 can be formed through the funnel wall of the upper funnel portion 363a. Optionally, the funnel 362 can include additional latching windows or voids at various spacing arrangements along the cannula, such as various angular orientations along the sidewall 391. The latching windows 370 can have any shape that can accommodates and permits access to portions of the latch mechanisms such as release buttons 338. In some embodiments, the latching windows 370 are larger or wider than the release buttons 338. The wider window can, for example, provide a tolerance in the rotational orientation at which the seal cartridge 340 can be assembled to the cannula 360, while still allowing the release buttons 338 to be accessed through the latching windows when the seal cartridge is assembled at different rotational or angular orientations about the longitudinal axis of the cannula.

Alternatively, or in combination with the latch mechanism voids, the cannula 360 can include one or more voids 371 to allow the fluid port 365 of the seal cartridge 340 to extend through the funnel wall. Advantageously, by allowing the fluid port 365 of the seal cartridge 340 to extend through the funnel wall, the seal cartridge 340 can be recessed within the funnel 362 while permitting access to the fluid port 365 for insufflation.

FIGS. 25A-25D illustrates the cannula assembly 300 of FIG. 24 during various states of assembly. With reference to FIGS. 25A-25D, during insertion of the seal cartridge 340 into the cannula 360, the seal cartridge 340 can be pivoted or tilted to allow the fluid port 365 to enter the window 370 prior to latching or otherwise engaging the seal cartridge 340 within the cannula. For example, the seal cartridge 340 can be pivoted or tilted into the funnel portion 362 of the cannula 360 in the sequence shown in FIGS. 25A-25D. During removal of the seal cartridge 340, the seal cartridge 340 can be disengaged by actuation release button(s) 338, and then pivoted to allow the fluid port 365 to pass through the window after the opposite portion of the seal cartridge 340 is removed. For example, the seal cartridge 340 can be pivoted or tilted away from the funnel portion 362 of the cannula 360 in the reverse of the sequence shown in FIGS. 25A-25D.

Figure 26:
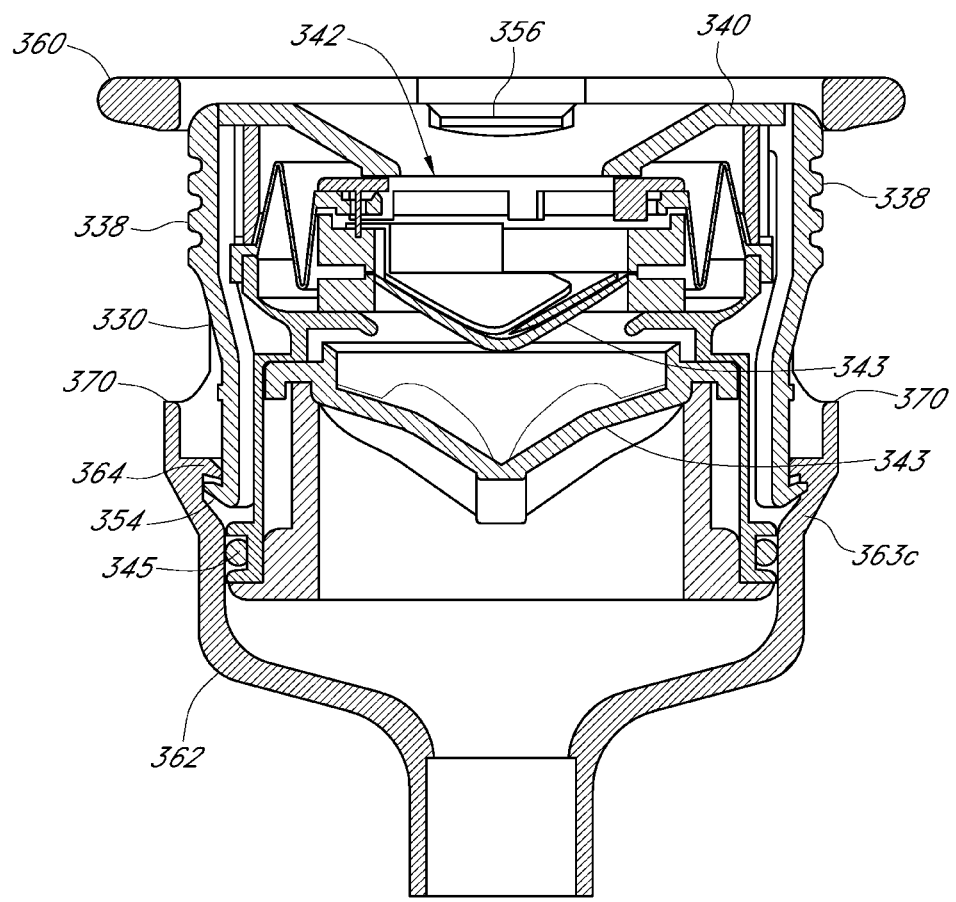
FIGS. 26 and 27 illustrate cross sections of the cannula assembly.
Figure 27:
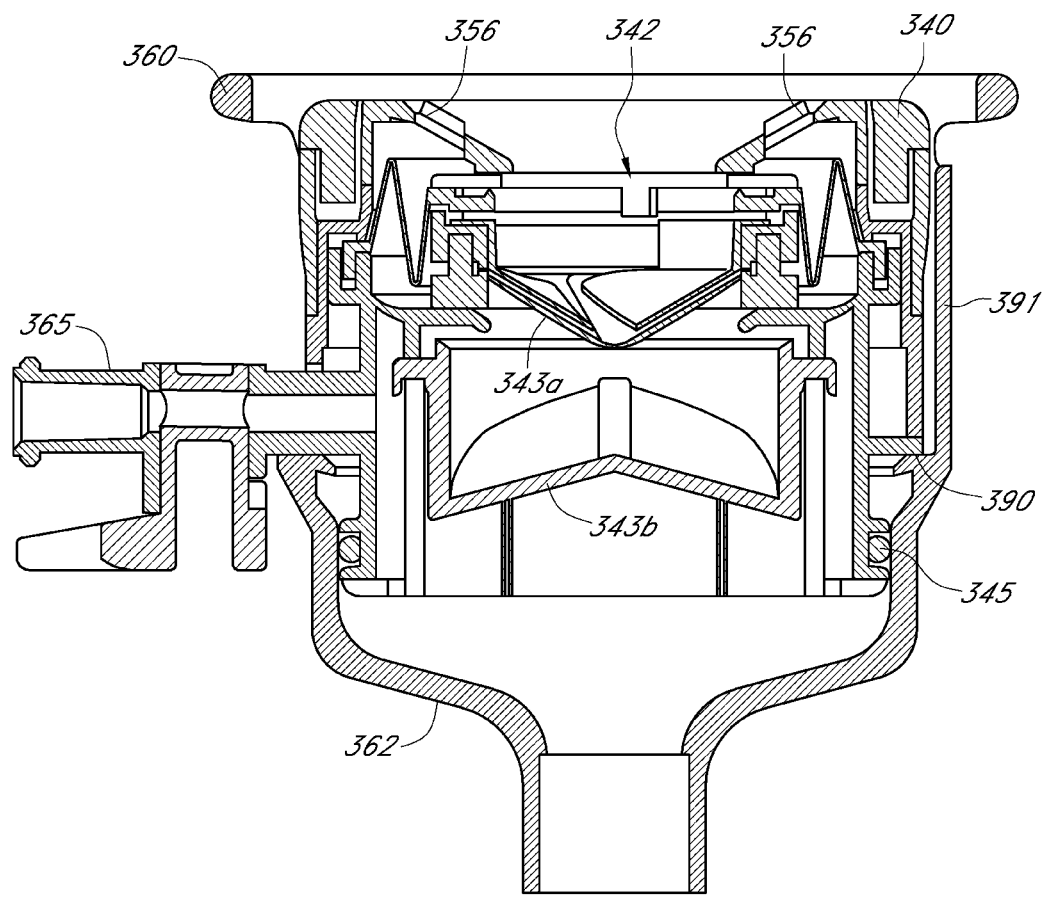

FIGS. 26 and 27 illustrate cross sections of the cannula assembly 300. FIG. 26 is a cross section taken through the seal latch mechanism 330. FIG. 27 is a cross section taken through the fluid port 365.

With reference to FIGS. 26 and 27, the seal cartridge 340 can latch or otherwise engage with the cannula 360. In the depicted example, the seal cartridge 340 includes a latching mechanism 330 to retain or otherwise couple the seal cartridge 340 with the cannula 360. As illustrated, the latching mechanism 330 extends from the seal cartridge 340 to engage with the cannula 360 to retain the seal cartridge 340 with the cannula 760. In the depicted example, latching mechanism 330 includes a latching hook 354 extending from the latching mechanism 330. The latching hook 354 can engage with features of the funnel 362, such as catch feature 364. Catch feature 364 can be, for example as seen in FIG. 26, an inner protruding lip the extends radially inward within the funnel portion 362. As illustrated, the latching hook 354 can engage the funnel at the transition portion 363c. The latching hook 354 also includes, for example, a lead-in surface at a distal end thereof to facilitate engagement of the seal cartridge 340 by moving the seal cartridge 340 distally until the latch mechanism snaps into engagement.

As seen in FIG. 27, the cannula funnel portion 360 can further include a ledge, lip, or stop member 390 that prevents the seal cartridge from being depressed too far in the distal direction when the seal cartridge 340 hits the stop member 390. In the depicted example, the stop member 390 is also disposed at the transition portion 363c.

Release buttons 338 are accessible through the cannula sidewall 391 via voids 370 extending through the sidewall. As seen in the example of FIG. 26, the latch mechanism can include a pair of opposing release buttons 338 on radially opposing sides of the cannula funnel portion 362, and the cannula funnel portion 362 can include a pair of corresponding voids to permit access to the release buttons 338. As can be appreciated, a clinician can depress the release buttons 338 to disengage the latching mechanism 330 from the cannula 360 to remove the seal cartridge 340. Optionally, the release button 338 can include a ridged or grooved portion to facilitate engagement of the release buttons 338 by the clinician.

In some embodiments, the latching mechanism 330 is biased outward to extend and engage with the cannula 360. Optionally, for example as seen in FIG. 26, the biasing member can be configured as a compliant tab or flexure that is integral to the latching mechanism to bias the hook features 354 radially outward against the cannula funnel portion. In the depicted example, depressing the release buttons 338 drives movement of the latch from an outward or engaged position to an inward or disengaged position.

It will be appreciated that although a particular form of the latch mechanism is shown, various modifications may be made to the latch mechanism. For example, while hook and catch engagement features are shown on the seal cartridge and cannula respectively, these features may be reversed, or the engagement features for securing the latch may take on other forms or geometries. Additionally or alternatively, while a compliant flexure based biasing mechanism is shown, coil springs, magnets, or other types of biasing members may be used. Additionally or alternatively, while the latch release is shown configured as push buttons, it is contemplated that sliders or other types of touch points can provide release mechanisms for disengaging the seal cartridge from the funnel portion.

Tools such as the obturator can be disposed on a top or proximal surface of the seal cartridge 340. In the illustrated embodiment, the seal cartridge 340 can include one or more latching slots 356 to allow the obturator to couple with the seal cartridge 340. In some embodiments, the latching mechanism of an obturator can extend into the latching slots 356 to couple the obturator with the seal cartridge 340.

In the depicted example, the seal cartridge 340 allows tools to extend through into the shaft lumen of the cannula 360 while maintaining insufflation within the patient cavity. In the depicted example, the seal cartridge 340 defines a central lumen 342 to allow tools to pass through the seal cartridge 340 and into the shaft lumen of the cannula 360.

As seen in FIGS. 26 and 27, the seal cartridge 340 includes a sealing system to maintain a hermetic seal within the lumen of the cannula. Seal cartridge 340 includes an inner seal 343 disposed within the central lumen 342 to maintain insufflation within the patient cavity. During operation, the inner seal 343 can prevent the escape of gas flow through the central lumen 342. The inner seal 343 can conform around the shaft of a tool, such as the obturator shaft, to prevent the escape of gas flow when a tool is passing through the seal cartridge 340. As can be appreciated, the inner seal 343 can also seal the central lumen 342 in the absence of a tool passing through the central lumen 342. The inner seal 343 can be formed from an elastomeric or otherwise resilient material, including but not limited to rubber, polymers, etc. In some applications, the inner seal 343 can include an upper sealing portion 343*a* that seals against the tool shaft when a tool is present, and a lower sealing portion 343*b* that provides a seal when the tool is not present. The lower sealing portion 343*b* can, for example, be implemented as a duckbill valve.

In some embodiments, the seal cartridge 340 includes an outer sealing member 345 disposed around an outer surface of the seal cartridge 340 to maintain insufflation within the patient cavity. During operation, the outer sealing member 345 can prevent the escape of gas flow between the seal cartridge 340 and the funnel 362 of the cannula 360. The outer sealing portion 345 can conform to the funnel walls of the funnel 362 to prevent the escape of gas flow. The outer sealing member 345 can be formed from an elastomeric or otherwise resilient material, including but not limited to rubber, polymers, etc. In the depicted example, the outer sealing member 345 is configured as an O-ring.

FIGS. 28-31 illustrate various configurations for the voids that may be employed in the cannula funnel portion to permit access to features of the seal cartridge.

Figure 28:
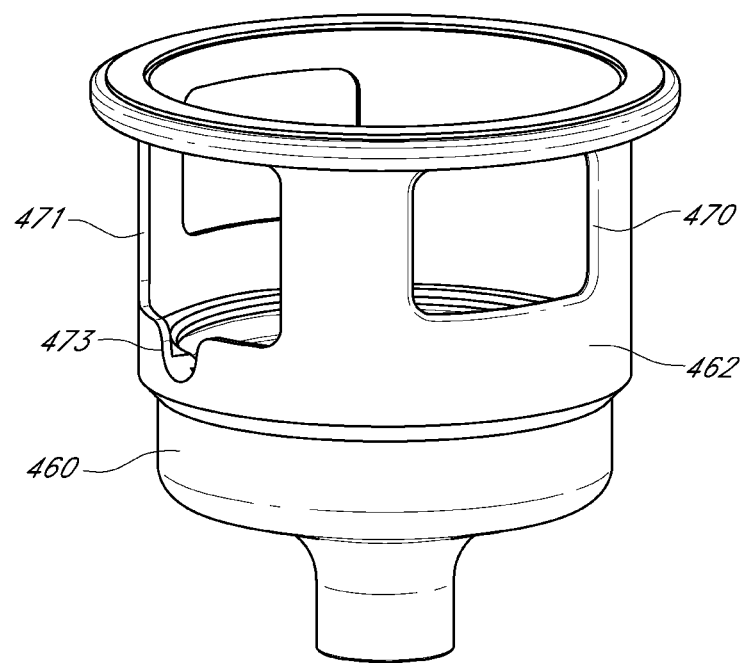
FIG. 28 illustrates a perspective view of a cannula that can be utilized with a seal cartridge or trocar assembly.

FIG. 28 illustrates a perspective view of a cannula 460 that can be utilized with a seal cartridge or trocar assembly as described above. In the depicted example, the fluid port window 471 includes features that further facilitate for alignment of the seal cartridge within the funnel.

As illustrated, the fluid port window 471 includes a notch 473 to receive the fluid port of the seal cartridge. Advantageously, the notch 473 can allow the seal cartridge to be rotationally aligned relative to the cannula 460. As illustrated, the notch 473 can be disposed at a lower edge of the fluid port window 471, providing tactile feedback when the fluid port lands within the notch 473. In some embodiments, the seal cartridge can recess further into the funnel 462 when the fluid port lands in the notch. Upon insertion, the notch 473 can prevent or resist the seal cartridge from rotating out of alignment from the aligned position. The notch 473 can have a generally semi-circular profile to receive the fluid port.

Additionally or alternatively, the notched fluid port window 471 can provide a visual indicator for the clinician to identify the fluid port window 471 relative to the other latching windows 470. Further, the clinician can orientate the seal cartridge for insertion into the cannula 460 based on the position of the fluid port window 471. Advantageously, by allowing the fluid port window 471 to be identified, the seal cartridge can be installed rapidly.

Figure 29:
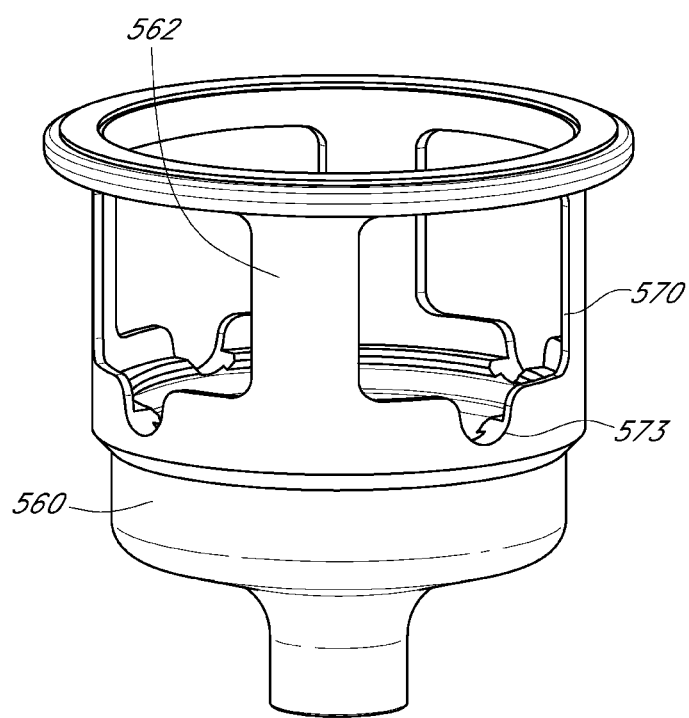
FIG. 29 illustrates a perspective view of a cannula that can be utilized with a seal cartridge or trocar assembly.

FIG. 29 illustrates a perspective view of a cannula 560 that can be utilized with a seal cartridge or trocar assembly as described above. In the depicted example, the cannula 560 can be configured to receive the seal cartridge in multiple rotational orientations.

As illustrated, the funnel 562 includes multiple voids or windows 570 formed through the funnel wall to allow either the latching mechanism or the fluid port of the seal cartridge to extend through the funnel wall. In some embodiments, each window 570 can have the same dimensions, allowing the latching mechanism or the fluid port to extend through any of the windows. In some embodiments, the seal cartridge can be introduced and coupled in various rotational arrangements relative to the cannula 560. Optionally, the windows 570 are symmetrically disposed. In some embodiments, the windows 570 are larger than the latching mechanism of the seal cartridge, allowing the seal cartridge to rotate within the funnel 562 while remaining engaged or otherwise axially retained.

In the depicted example, each window 570 includes a notch 573 to receive the fluid port of the seal cartridge. As described herein, the notch 573 can allow the seal cartridge to be rotationally aligned relative to the cannula 560 by aligning the fluid port within the respective window 570. Therefore, the seal cartridge can be inserted in various rotational orientations, permitting the fluid port of the seal cartridge to extend through any of the windows 570 and land within a respective notch 573, aligning the fluid port and therefore the seal cartridge relative to the window 570. In another example, each of the windows can be symmetrically arranged without a notch in each window. In the depicted example, four windows are included to facilitate engagement with a seal cartridge where the seal cartridge has a fluid port offset by 90 degrees with respect to a pair of opposing seal latch buttons. Advantageously, by allowing the various rotational orientations of the seal cartridge relative to the cannula 560, the seal cartridge can be installed more rapidly.

Figure 30:
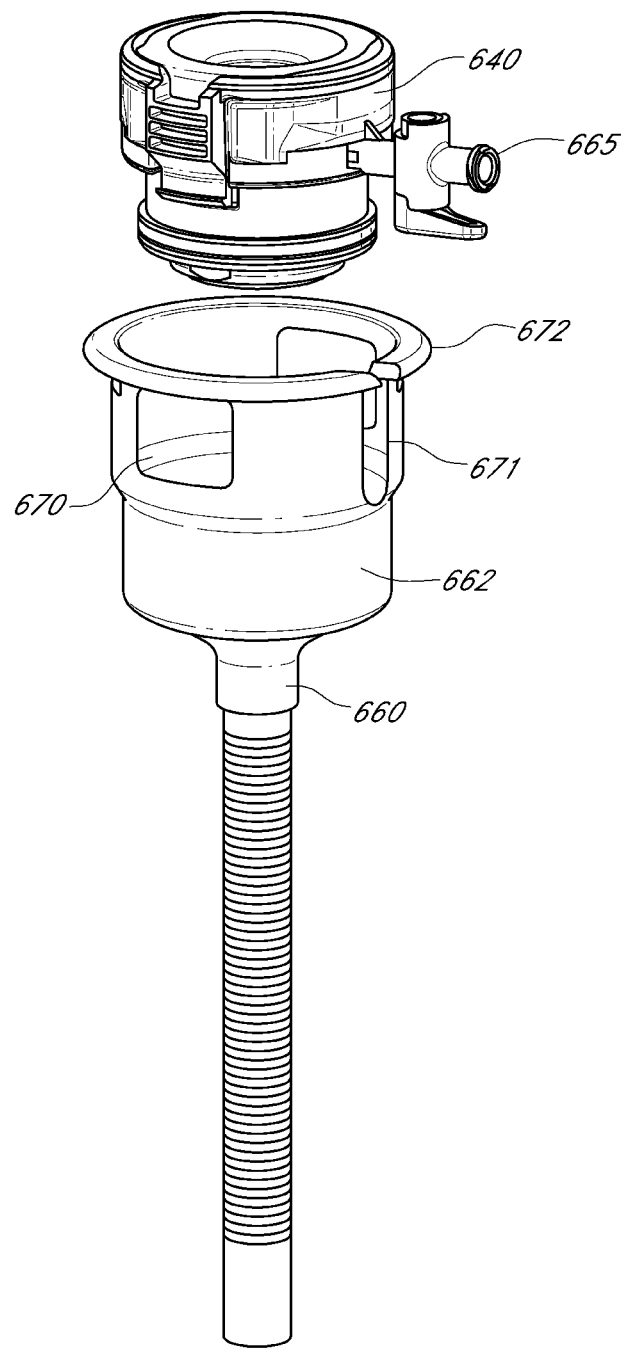
FIGS. 30 and 31 each illustrate a perspective view of a cannula that can be utilized with a seal cartridge or trocar assembly as described above.
Figure 31:
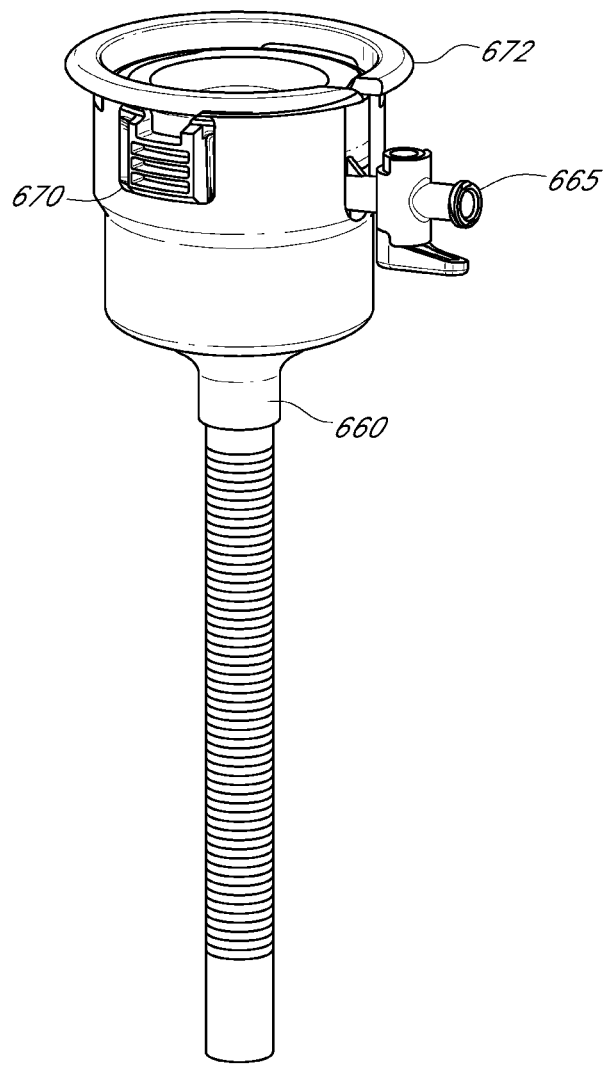

FIGS. 30 and 31 each illustrate a perspective view of a cannula 660 that can be utilized with a seal cartridge or trocar assembly as described above. FIG. 30 illustrates the cannula and seal cartridge in an uncoupled configuration, while FIG. 31 illustrates the cannula 660 of FIG. 30 with the seal cartridge coupled to the cannula. With reference to FIGS. 30 and 31, in some embodiments, the cannula 660 can include an axially extending slot 671 to allow the fluid port 665 of the seal cartridge 640 to extend through the funnel wall. As illustrated, the slot 671 can extend from a proximal end of the funnel 662 and extend distally from the brim 672 and through at least a portion of the funnel wall. The slot 671 can form a discontinuity in the circular profile of the brim 672 and the funnel wall. As can be appreciated, the slot 671 can rotationally index the seal cartridge 640 as it is inserted into the funnel 662 to rotationally align the seal cartridge 640 relative to the cannula 660. Advantageously, the seal cartridge 640 can be inserted into the cannula 660 without pivoting or tilting.

Similar to cannula 560, the cannula 660 can include multiple voids or windows 670 formed through the funnel wall to allow the latching mechanism of the seal cartridge 640 to extend through the funnel wall. As illustrated, the windows 670 can be disposed approximately 180 degrees apart from each other. Further, the windows 670 can be evenly spaced relative to the slot 671, such that each window 670 is disposed approximately 90 degrees apart from the slot 671. In some embodiments, the windows 670 can be disposed to allow various rotational arrangements of the seal cartridge 640 relative to the cannula 660.

It will be appreciated from the forgoing examples that the present disclosure contemplated various features that may be employed in cannula assemblies. In some embodiments, a cannula includes a funnel portion having a sidewall, a tubular portion extending distally from the funnel portion, and one or more voids in the side wall of the funnel portion that permit access to a seal cartridge through the sidewall.

In some embodiments, the cannula includes a funnel portion having a sidewall and a circumferential rim, a tubular portion extending distally from the funnel portion, and a cartridge slot formed in the funnel portion, the cartridge slot comprising a discontinuity in the rim of the funnel portion that opens to a void in the side wall of the funnel portion to permit access to a fluid port of a seal cartridge through the sidewall.

In some embodiments, a method of assembling a trocar assembly includes inserting a fluid port of a seal cartridge through a void of a funnel portion of a cannula, the cannula funnel portion having a sidewall and a tubular portion extending distally from the funnel portion, the void of the cannula funnel portion extending through the side wall of the funnel portion, and coupling the seal cartridge to the cannula within the cannula funnel portion.

Figure 32:
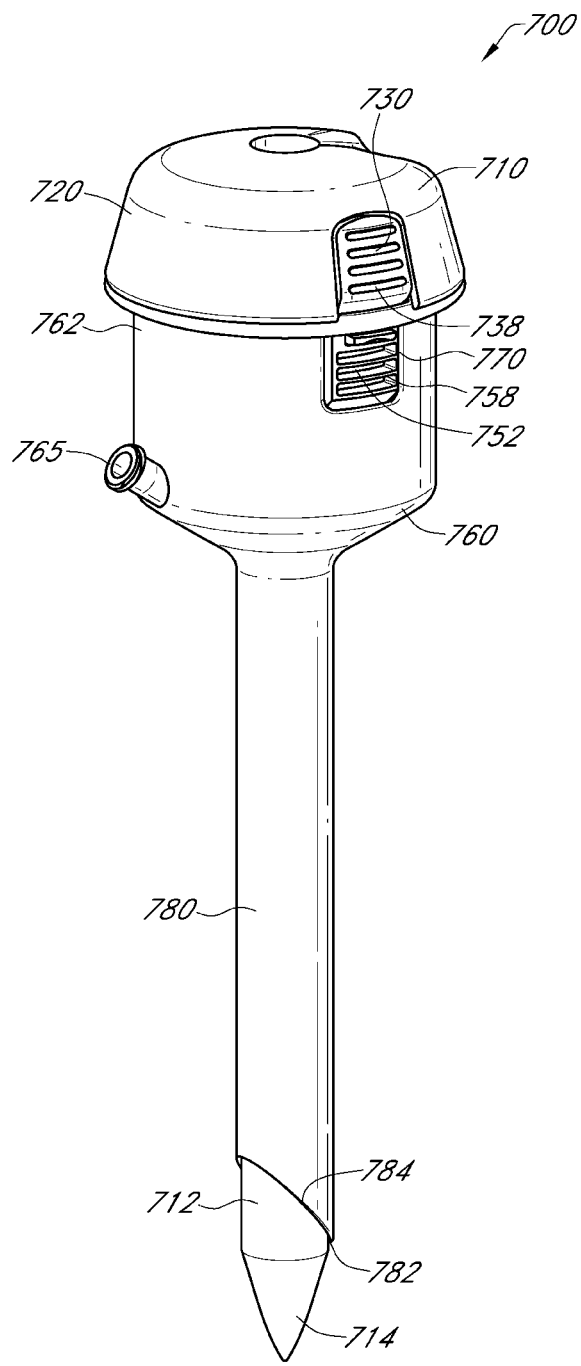
FIG. 32 illustrates a perspective view of a trocar assembly in an assembled state.
Figure 33:
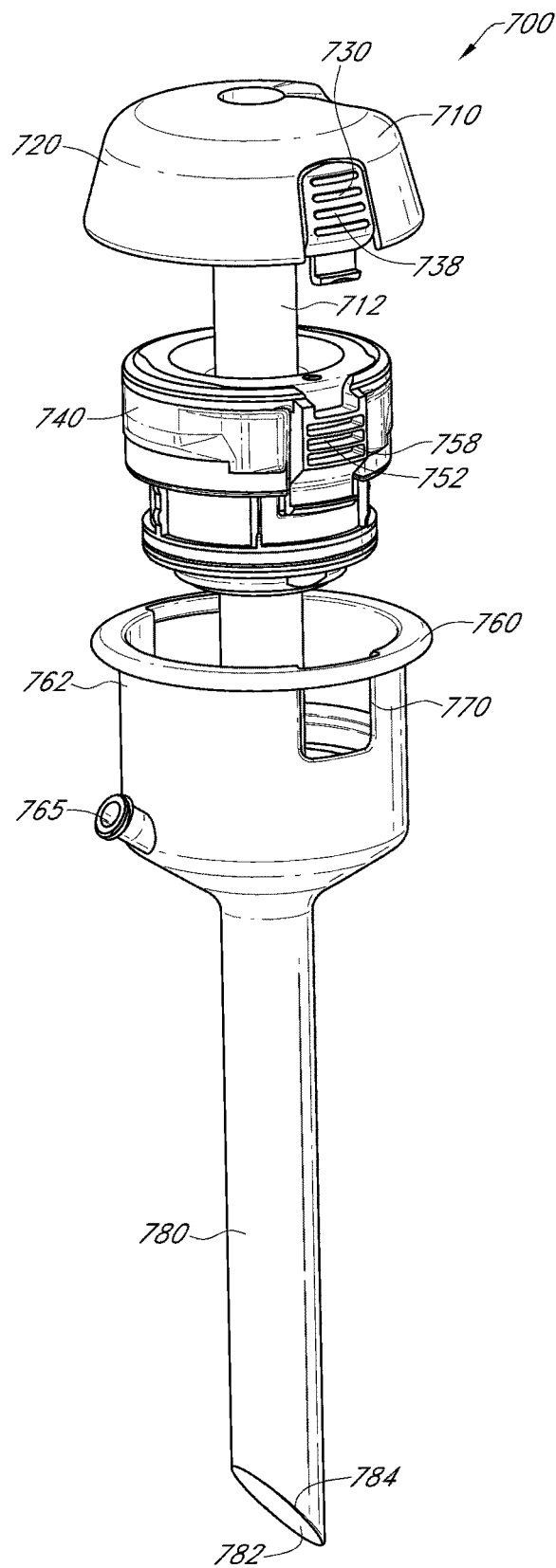
FIG. 33 illustrates a perspective view of the trocar assembly of FIG. 32 in a semi-assembled state.
Figure 34:
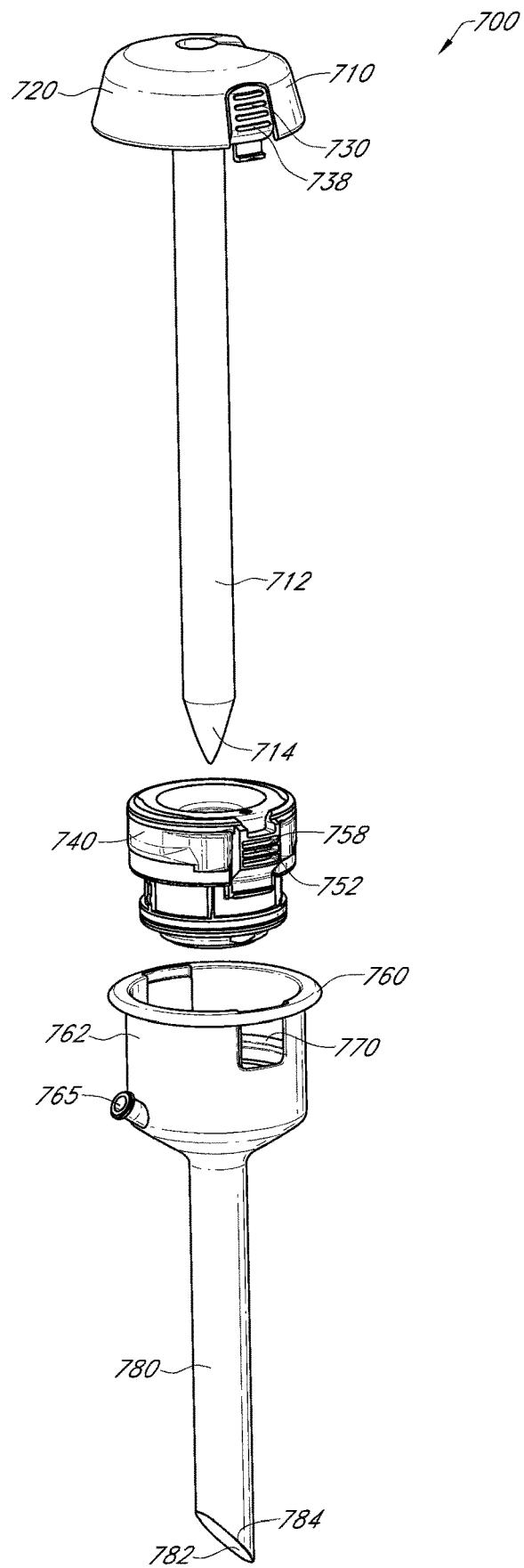
FIG. 34 illustrates a perspective view of the trocar assembly of FIG. 32 in an exploded state.

In some embodiments, trocar assemblies can be configured to allow tools, such as obturators, to be directly latched to a cannula. FIG. 32 illustrates a perspective view of a trocar assembly 700 in an assembled state. FIG. 33 illustrates a perspective view of the trocar assembly 700 of FIG. 32 in a semi-assembled state. FIG. 34 illustrates a perspective view of the trocar assembly 700 of FIG. 32 in an exploded state. As can be appreciated, the trocar assembly 700 can include features that are similar to trocar assembly 200. Therefore, unless noted, similar features may be referred to with similar reference numerals.

In the depicted example, latching mechanism 730 of the obturator 710 can allow the obturator 710 to be coupled or released from the cannula 760. In some embodiments, the latching mechanism 730 can extend from the upper portion 720 of the obturator 710 to releasably engage with other portions of the trocar assembly 700. In some embodiments, the latching mechanism 730 includes one or more release buttons 738 that can be operated to release the latching mechanism 730 and disengage the obturator from the cannula 760.

In the illustrated embodiment, the latching mechanism 730 can extend into the latching windows 770 defined in the cannula 760 to couple the obturator 710 with the cannula 760. The latching mechanism 730 of the obturator 710 can be biased outward to retain coupling between the obturator 710 and the cannula 760 or other portions of the trocar assembly 700.

In some applications, the trocar assembly 700 can allow for insufflation of the patient cavity during procedures to provide access within the patient cavity while minimizing trauma to the patient. In the depicted example, gas can be introduced into the patient cavity via a gas port 765 formed in the cannula 760, but the gas port 765 may alternatively be configured as part of the removable seal cartridge 740, as in the earlier described configurations of FIGS. 24-31. In some embodiments, the gas port 765 is in fluid communication with the cannula lumen 782.

The trocar assembly 700 can include a seal cartridge 740 to maintain insufflation within the patient cavity after the introduction of gas into the patient cavity. The seal cartridge 740 can be coupled to the cannula 760 to sealingly isolate the cannula lumen 782 from the environment to maintain insufflation within the patient cavity. During operation, the seal cartridge 740 can maintain isolation of the patient cavity while permitting tools, such as the obturator 710 to pass through a passage of the seal cartridge 740. Further, the seal cartridge 740 can sealingly engage against the cannula funnel 762 to maintain insufflation of the patient cavity. As illustrated, the seal cartridge 740 can be seated within the funnel portion 762 of the cannula 760. In some embodiments, the seal cartridge 740 is fully seated within the funnel portion 762 and does not extend beyond the funnel portion 762.

In some applications, the seal cartridge 740 can be removed from the cannula 760. As described herein, the seal cartridge 740 and the cannula 760 may have differing useful lives facilitated by the removable engagement of the seal cartridge 740 with respect to the cannula 760. For example, the seal cartridge 740 can be configured as a single use disposable device while the cannula 760 can be configured to be sterilized and re-used. In some applications, when the seal cartridge 740 is removed from the cannula 760, the insufflation gas is released from the patient cavity. As can be appreciated, it is undesired to release the insufflation gas from the patient cavity unexpectedly or otherwise prematurely, as loss of insufflation can increase patient trauma and decrease access within the patient cavity.

As described herein, a latching mechanism 752 of the seal cartridge 740 can allow the seal cartridge 740 to be coupled or released from the cannula 760. In some embodiments, the latching mechanism 752 can releasably engage with other portions of the trocar assembly 700. In the illustrated embodiment, the latching mechanism 752 can extend from the body of the seal cartridge 740 into the latching windows 770 defined in the cannula 760 to couple the seal cartridge 740 with the cannula 760. The latching mechanism 752 of the seal cartridge 740 can be biased outward to retain coupling between the obturator 710 and the seal cartridge 740. In some embodiments, the obturator 710 can be latched to the seal cartridge 740.

In some embodiments, the latching mechanism 752 includes one or more release buttons 758 that can be operated to release the latching mechanism 752 and disengage the seal cartridge 740 from the cannula 760. Optionally, the release button 738 of the obturator 710 can be rotationally aligned with the release button 758 of the seal cartridge 740.

Advantageously, the trocar assembly 700 is configured to prevent the inadvertent removal of the seal cartridge 740, preventing inadvertent loss of insufflation. In the depicted example, when the obturator 710 is coupled to the cannula 760, the seal cartridge 740 is retained between the upper portion of the obturator 710 and the cannula funnel 762. Therefore, the seal cartridge 740 cannot be inadvertently removed from the cannula 760 prior to the removal of the obturator 710 from the cannula 760.

Figure 35:
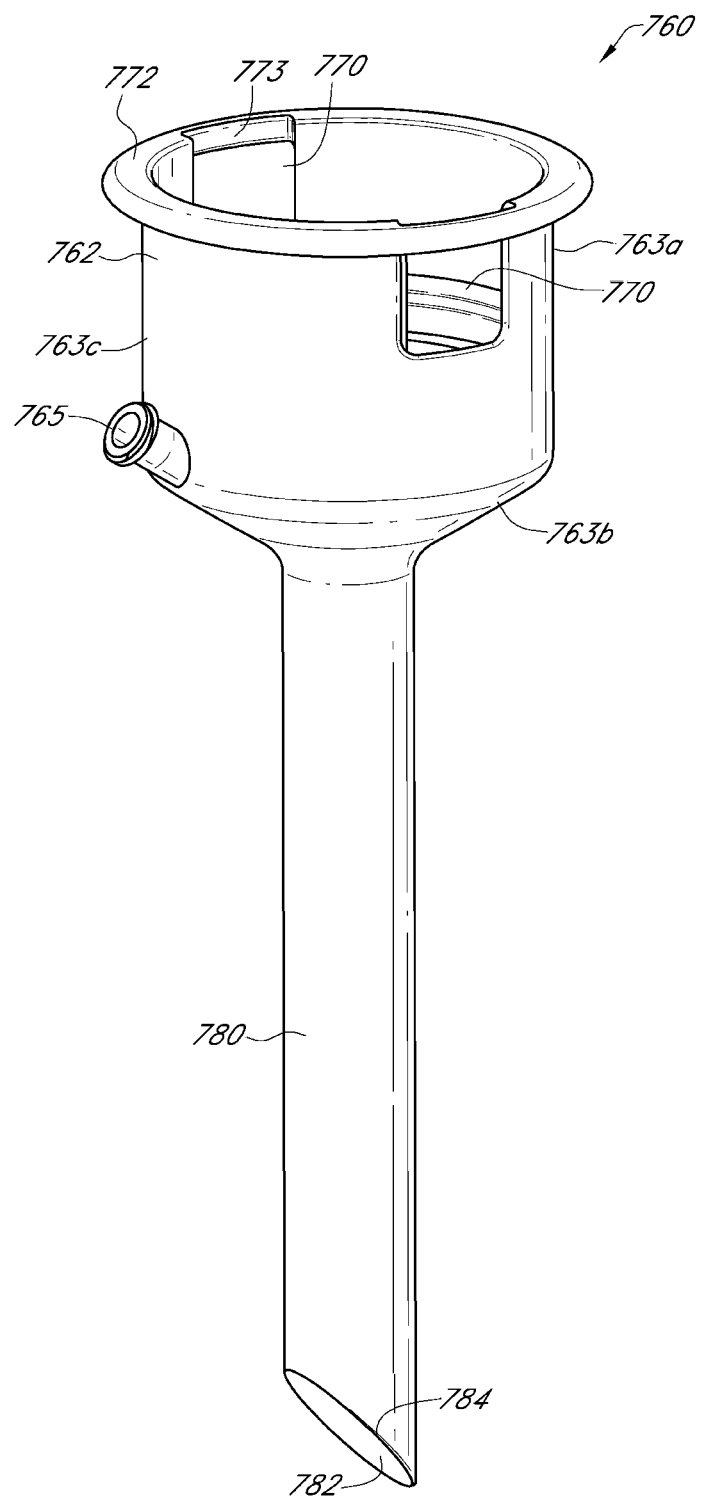
FIG. 35 illustrates a perspective view of the cannula of the trocar assembly of FIG. 32.

FIG. 35 illustrates a perspective view of the cannula of the trocar assembly of FIG. 32. In the depicted example, the geometry of the funnel 762 can permit portions of tools, such as the obturator 710, and/or the seal cartridge 740 to be disposed at least partially within the funnel 762 of the cannula 760. As can be appreciated, by disposing portions of the obturator 710 and/or the seal cartridge 740 within the funnel 762, the obturator 710 and/or the seal cartridge 740 can move together with the cannula 760 and reduce the assembled size of the trocar assembly 700. In some embodiments, the obturator 710 and/or the seal cartridge 740 can be coupled to the cannula 760 via the funnel 762.

In some embodiments, the seal cartridge 740 can be disposed within the lower tapered portion 763b and a portion of the upper tapered portion 763a of the funnel 762. As illustrated in FIG. 33, the funnel walls of the funnel 762 can extend beyond the seal cartridge 740 when the seal cartridge 740 is seated within the funnel 762 to allow the seal cartridge 740 to be recessed within the funnel 762. In some embodiments, the seal cartridge 740 can extend beyond the funnel 762.

In some embodiments, the funnel 762 can include features to allow the seal cartridge 740 to be retained or otherwise coupled to the funnel 762. For example, in some applications, the engagement or latching mechanism of the seal cartridge 740 can engage the transition portion 763c of the funnel 762 to axially retain the seal cartridge 740 within the funnel 762. Optionally, the seal cartridge 740 can engage with a recess or protrusions of the transition portion 763c.

In some applications, the engagement or latching mechanism of the seal cartridge 740 can engage with latching windows 770 formed through the funnel wall. For example, latching mechanism of the seal cartridge 740 can extend through the latching windows 770 of the cannula 760 to retain the seal cartridge 740 within the cannula 760. In some embodiments, the funnel 762 can include two latching windows 770 disposed radially across from each other. As illustrated, the latching windows 770 can be formed through the funnel wall of the upper tapered portion 763a. Optionally, the funnel 762 can include additional latching windows 770 are various spacing arrangements. The latching windows 770 can have a generally rectangular shape. As can be appreciated, the seal cartridge 740 can engage with other portions of the cannula 760 and/or other components of the trocar assembly 700.

Further, an upper portion or head portion 720 of the obturator 710 can be at least partially disposed within the upper tapered portion 763a of the funnel 762. In some embodiments, the funnel 762 can include features to allow the obturator 710 to be retained or otherwise coupled to the funnel 762. For example, in some applications, the engagement or latching mechanism of the obturator 710 can releasably engage the brim 772 of the funnel 762 to axially retain the obturator 710 relative to the cannula 760. The obturator 710 can engage with a protruding portion of the brim 772. Optionally, the brim 772 can include recessed portions 773 to accommodate features of the engagement or latching mechanism of the obturator 710.

In some applications the engagement or latching mechanism of the obturator 710 can also engage with latching windows 770 formed through the funnel wall. For example, the latching mechanism of the obturator 710 can extend through the latching windows 770 of the cannula 760 to retain obturator 710 relative to the cannula 760. Optionally, the brim 772 of the cannula 760 can define an edge or boundary of the latching windows 770. As can be appreciated, the obturator 710 can engage with other portions of the cannula 760 and/or other components of the trocar assembly 700.

As described herein, the cannula 760 can allow for insufflation of the patient cavity. In the depicted example, the cannula 760 includes a gas port 765 formed at a lower portion of the funnel 762 that allows for gas to flow into the shaft lumen 782. In some embodiments, the gas port 765 is in fluid communication with the shaft lumen 782. The gas port 765 can be sealed or isolated from the upper portion of the funnel 762 by the seal cartridge 740.

Figure 36:
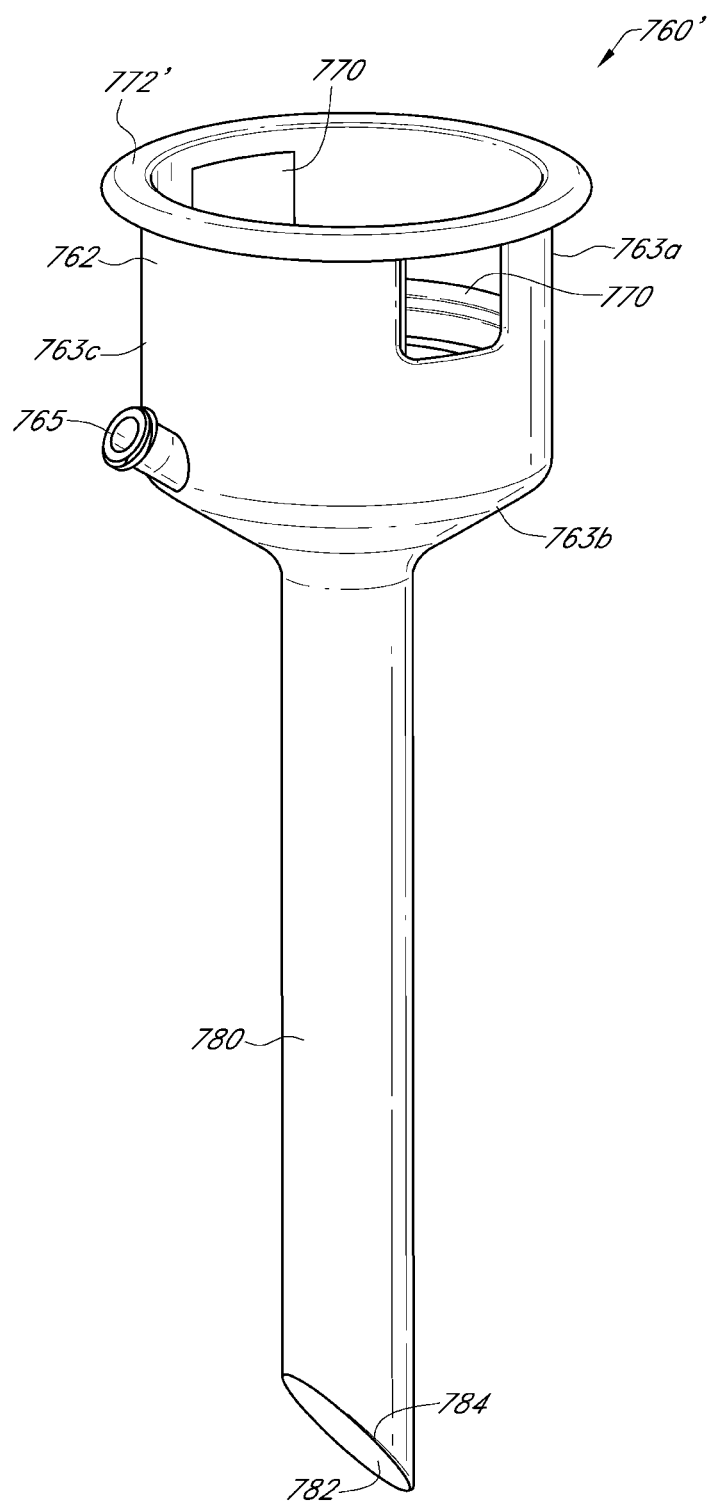
FIG. 36 illustrates a perspective view of another embodiment of a cannula for use with the trocar assembly of FIG. 32.

FIG. 36 illustrates a perspective view of another embodiment of a cannula for use with the trocar assembly of FIG. 32. Similar to cannula 760, the cannula 760' allows for the engagement or latching mechanism of the obturator 710 to releasably engage the brim 772' of the funnel 762 to axially retain the obturator 710 relative to the cannula 760'. In the depicted example, the brim 772' can maintain a constant thickness or inner diameter across the circumference of the brim 772'.

Figure 37:
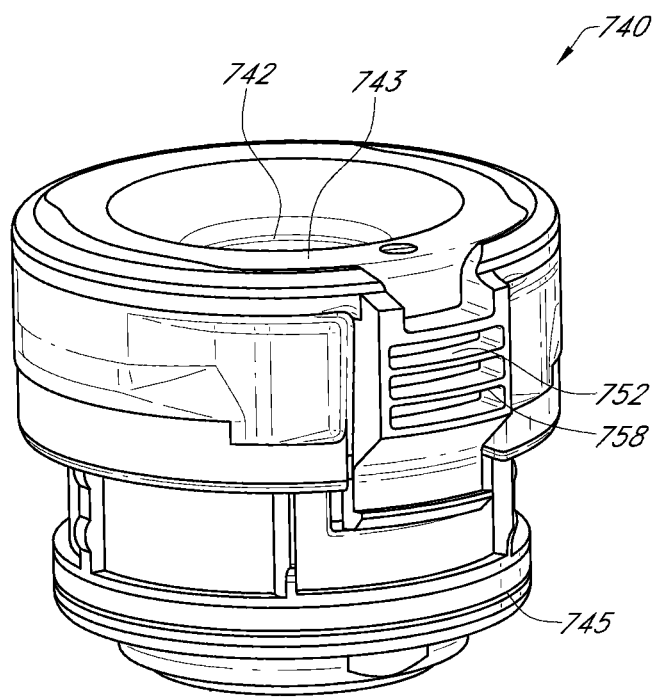
FIG. 37 illustrates a perspective view of the seal cartridge of the trocar assembly of FIG. 32.

FIG. 37 illustrates a perspective view of the seal cartridge of the trocar assembly of FIG. 32. In the depicted example, the seal cartridge 740 allows tools to through into the shaft lumen 782 of the cannula 760 while maintaining insufflation within the patient cavity.

In the depicted example, the seal cartridge 740 defines a central lumen 742 to allow tools, such as the obturator 710 to pass through the seal cartridge 740 and into the shaft lumen 782 of the cannula 760.

In some embodiments, the seal cartridge 740 includes an inner sealing member 743 disposed within the central lumen 742 to maintain insufflation within the patient cavity. During operation, the inner sealing member 743 can prevent the escape of gas flow through the central lumen 742. The inner sealing member 743 can conform around the shaft of a tool, such as the obturator shaft 712 to prevent the escape of gas flow when a tool is passing through the seal cartridge 740. As can be appreciated, the inner sealing member 743 can expand to seal the central lumen 742 in the absence of a tool passing through the central lumen 742. The inner sealing member 743 can be formed from an elastomeric or otherwise resilient material, including but not limited to rubber, polymers, etc. In some applications, the inner sealing member 743 can be implemented as a duckbill valve.

In some embodiments, the seal cartridge 740 includes an outer sealing member 745 disposed around an outer surface of the seal cartridge 740 to maintain insufflation within the patient cavity. During operation, the outer sealing member 745 can prevent the escape of gas flow between the seal cartridge 740 and the funnel 762 of the cannula 760. The outer sealing member 745 can conform to the funnel walls of the funnel 762 to prevent the escape of gas flow. The outer sealing member 745 can be formed from an elastomeric or otherwise resilient material, including but not limited to rubber, polymers, etc.

Figure 38:
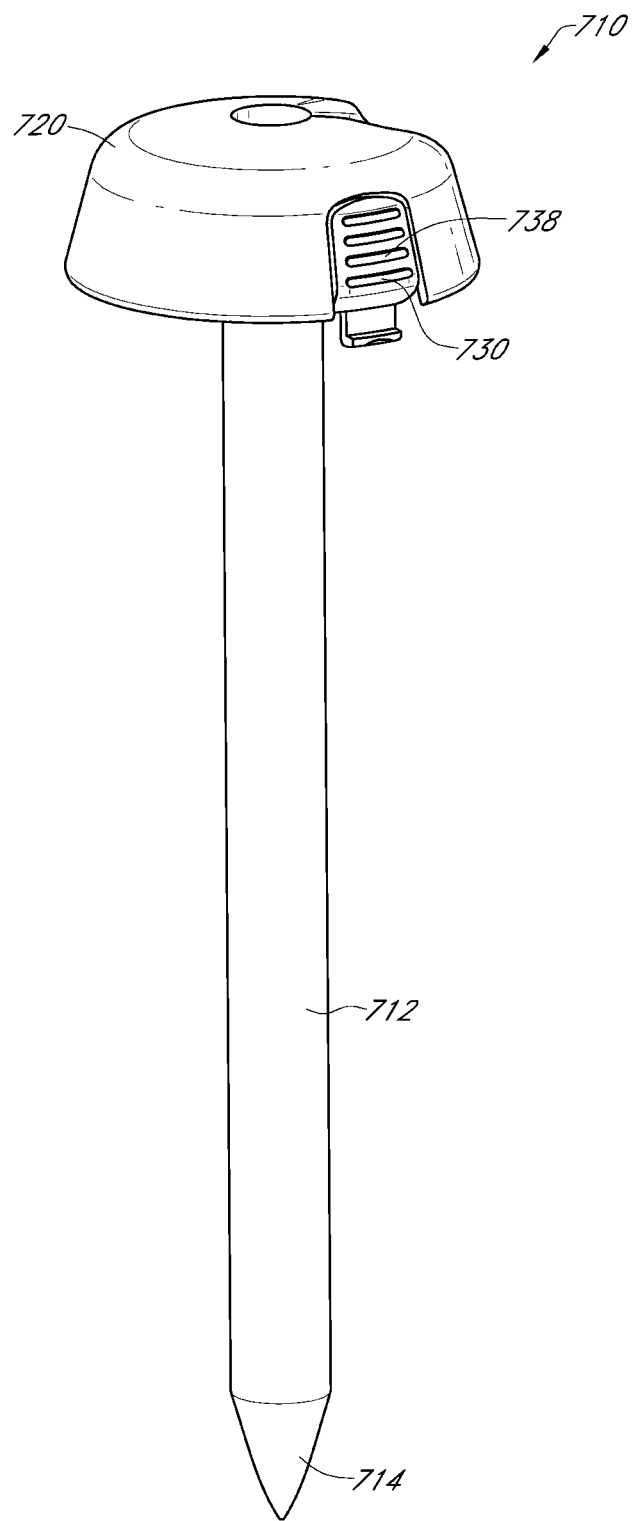
FIG. 38 illustrates a perspective view of the obturator of the trocar assembly of FIG. 32.

FIG. 38 illustrates a perspective view of the obturator of the trocar assembly of FIG. 32.

In the depicted example, the obturator 710 can displace tissue to allow the trocar assembly 700 to be inserted into the patient cavity. As illustrated, the obturator 710 includes a shaft 712 that extends from an upper portion 720 of the obturator 710. In some applications the shaft 712 can extend beyond the end portion 784 of the cannula 760 when the obturator 710 is coupled to the cannula 760. The shaft 712 can have a generally cylindrical shape that allows the obturator 710 to rotate within the patient cavity.

The shaft 712 can include a tapered, beveled, or otherwise pointed end or tip 714. During operation, by advancing the obturator 710, the shaft 712 can pierce, displace, or otherwise dissect the patient tissue to allow the obturator 710 and the coupled cannula 760 to access the patient cavity.

Optionally, the upper portion 720 can be utilized by clinicians as a handle to apply force or otherwise advance the obturator 710 and/or the trocar assembly 700 generally. As illustrated, the upper portion 720 of the obturator 710 can have a generally larger radius than the shaft 712 to allow a clinician to easily apply more force to the shaft 712. Further, the upper portion 720 can include a grasping portion or a planar surface to allow the clinician to advance the obturator 710. In some embodiments, as described herein, the enlarged geometry of the upper portion 720 can retain the seal cartridge 740 within the cannula 760 when the obturator 710 is also coupled to the cannula 760.

Figure 39:
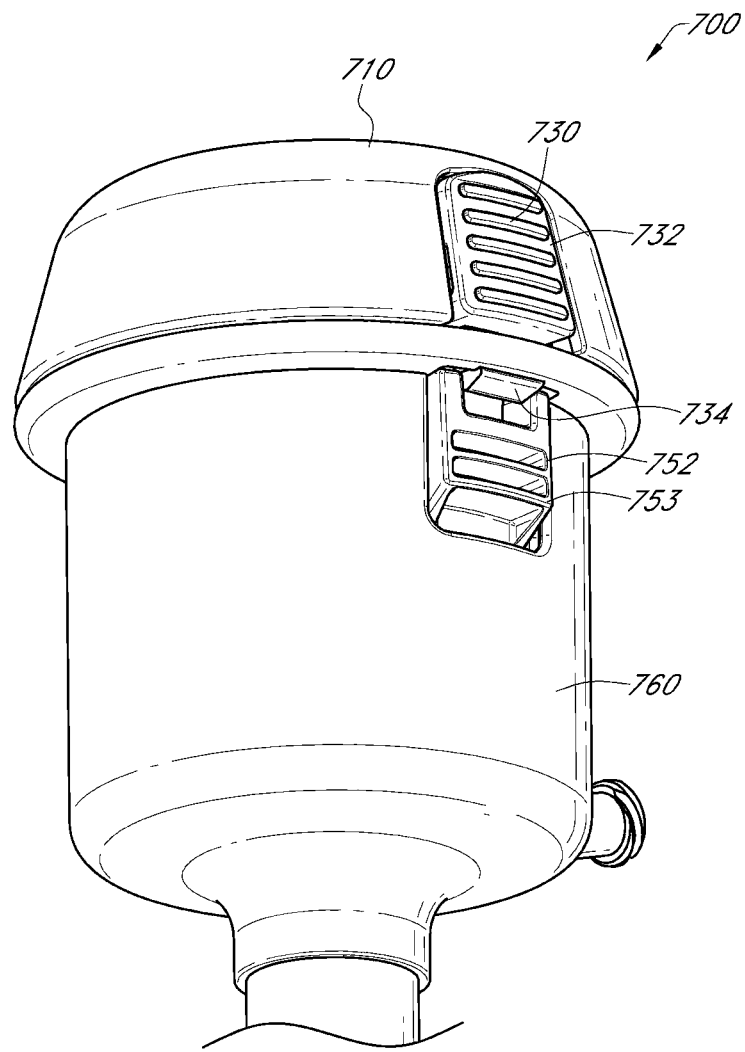
FIG. 39 illustrates a perspective view of the latch mechanism of the obturator and the latch mechanism of the seal cartridge of the trocar assembly of FIG. 32.
Figure 40:
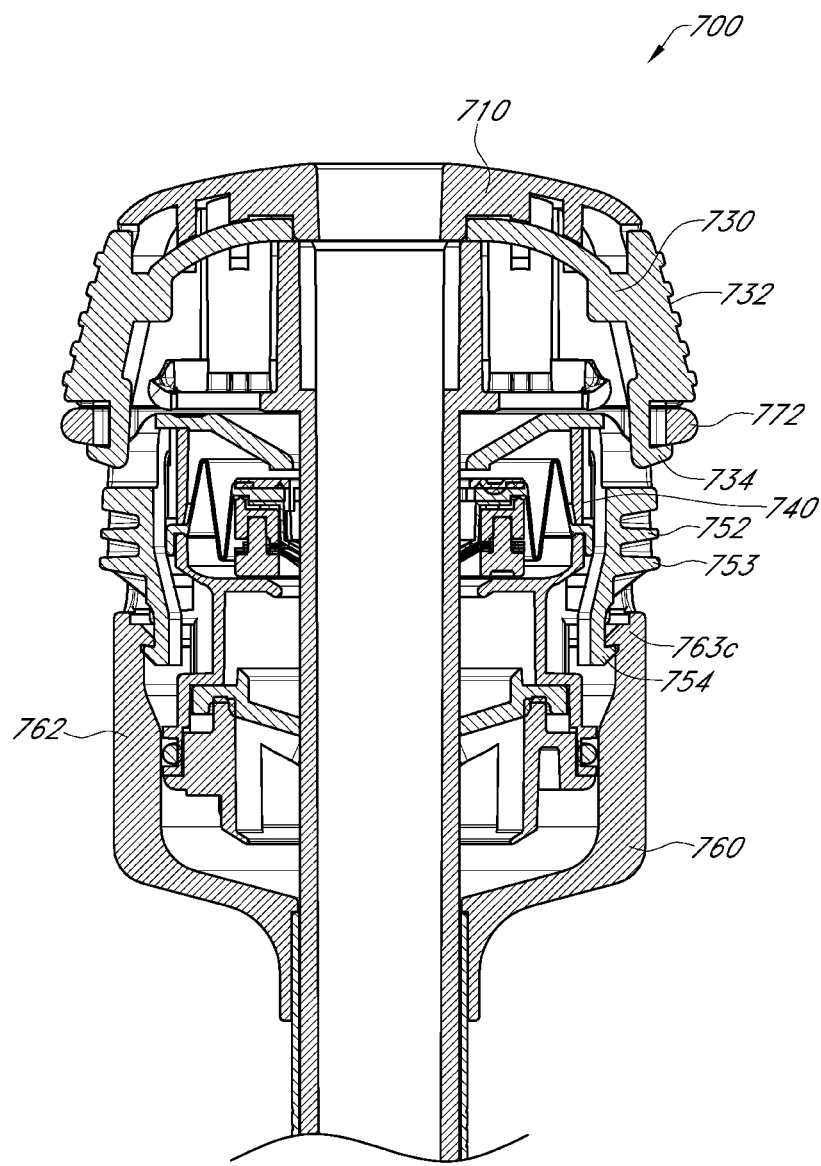
FIG. 40 illustrates a cross sectional view of the trocar assembly of FIG. 32 with the latch mechanism of the obturator shown in an engaged position.

FIG. 39 illustrates a perspective view of the latch mechanism of the obturator and the latch mechanism of the seal cartridge of the trocar assembly of FIG. 32. FIG. 40 illustrates a cross sectional view of the trocar assembly of FIG. 32 with the latch mechanism of the obturator shown in an engaged position. With reference to FIGS. 39 and 40, the seal cartridge 740 and the obturator 710 can latch or otherwise engage with the cannula 760.

In the depicted example, the seal cartridge 740 includes a latching mechanism 752 to retain or otherwise couple the seal cartridge 740 with the cannula 760. As illustrated, the latching mechanism 752 extends from the seal cartridge 740 to engage with the cannula 760 to retain the seal cartridge 740 with the cannula 760. In some embodiments, the latching mechanism 752 includes a latching hook 754 extending from the latching mechanism 752. The latching hook 754 can engage with features of the funnel 762, such as the transition portion 763*c* to engage the cannula 760.

The latching mechanism 750 can further include an extension portion 753. The extension portion 753 can engage with features of the funnel 762. For example, the extension portion 753 can extend through the latching windows 770 of the cannula 760. In some embodiments, the latching mechanism 752 includes a biasing member to bias the latching mechanism 752 outward to extend and engage with the cannula 760. Optionally, the biasing member can be integral to the latching mechanism.

As can be appreciated, a clinician can depress the extension portions 753 to disengage the latching mechanism 752 from the cannula 760 to remove the seal cartridge 740. Optionally, the extension portion 753 can include a ridged or grooved portion to allow a clinician to engage the latching mechanism 752. In some embodiments, portions of the seal cartridge 740 can extend over the cannula funnel 762 to engage with or otherwise latch to an outer edge of the cannula brim 772 or other features of the cannula 760.

In the depicted example, the obturator 710 includes a latching mechanism 730 to retain or otherwise couple the obturator 710 with the cannula 760. As illustrated, the latching mechanism 730 extends from the obturator 710 to engage with the cannula 760 to retain the obturator 710 with the cannula 760. In some embodiments, the latching mechanism 730 includes a latching hook 734 extending from the latching mechanism 730. The latching hook 734 can engage with features of the funnel 762, such as the brim 772 to engage the cannula 760.

The latching mechanism 730 can further include an extension portion 732. The extension portion 732 can engage with features of the funnel 762. For example, the extension portion 732 can extend through the latching windows 770 of the cannula 760. In some embodiments, the latching mechanism 730 includes a biasing member to bias the latching mechanism 730 outward to extend and engage with the cannula 760. Optionally, the biasing member can be integral to the latching mechanism.

As illustrated, the latching mechanism 730 of the obturator 710 and the latching mechanism 752 of the seal cartridge 740 can be rotationally aligned. Here, that rotational alignment allows the windows 770 to serve a dual purpose, where they not only provide access to the seal cartridge release buttons, but also serve as a feature in the cannula funnel 762 that can engage with the latching hooks 734 of the latching mechanism 730 of the obturator 710. Accordingly, this avoids a need to manufacture an additional latching feature on the cannula funnel 762 for engagement of the latching mechanism 730 of the obturator 710. In some embodiments, the latching mechanism 730 of the obturator 710 and the latching mechanism 752 of the seal cartridge 740 can be rotationally spaced apart.

In some applications, because the obturator 710 is directly latched to the cannula 760, the trocar assembly 700 can be configured to prevent the inadvertent removal of the seal cartridge 740, preventing inadvertent loss of insufflation. In the depicted example, when the obturator 710 is coupled to the cannula 760, the upper portion 720 of the obturator 710 retains the seal cartridge 740 within the funnel 762, preventing the seal cartridge 740 from being removed from the cannula 760 prior to the removal of the obturator 710 from the cannula 760. As can be appreciated, the obturator 710 can retain the seal cartridge 740 within the funnel 762 upon inadvertent release of the latching mechanism 752 of the seal cartridge 740. In some embodiments, portions of the obturator 710 can extend over the cannula funnel 762 to engage with or otherwise latch to an outer edge of the cannula brim 772 or other features of the cannula 760.

Figure 41:
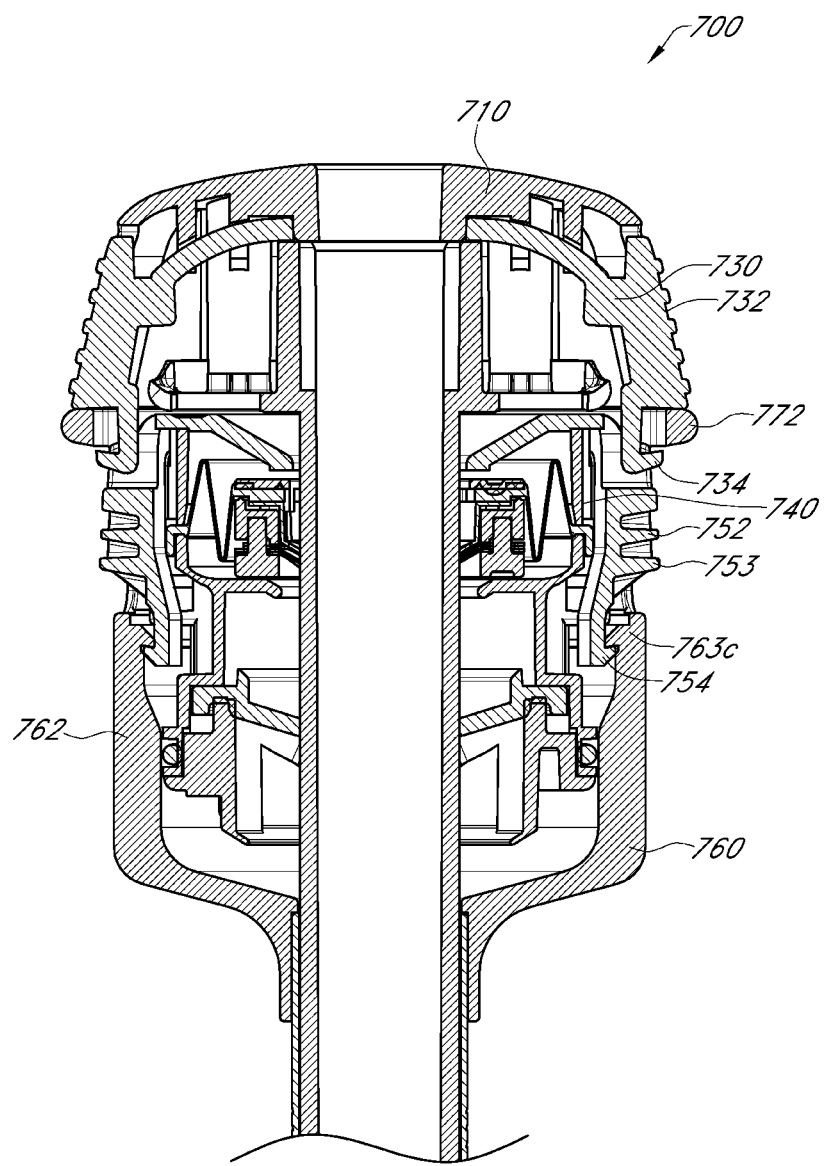
FIG. 41 illustrates a cross sectional view of the trocar assembly of FIG. 32 with the latch mechanism of the obturator shown in a disengaged position.

FIG. 41 illustrates a cross sectional view of the trocar assembly of FIG. 32 with the latch mechanism of the obturator shown in a disengaged position. With reference to FIG. 41, a clinician can depress the extension portions 732 of the latching mechanism 730 to disengage the latching mechanism 730 from the cannula 760 to remove the obturator 710. Optionally, the extension portion 732 can include a ridged or grooved portion to allow a clinician to engage the latching mechanism 730. Upon disengaging the obturator 710 from the cannula 760, a clinician can depress the extension portions 753 to disengage the latching mechanism 752 from the cannula 760 to remove the seal cartridge 740. Optionally, the seal cartridge 740 and the obturator 710 an be removed from the cannula 760 together.

Figure 42:
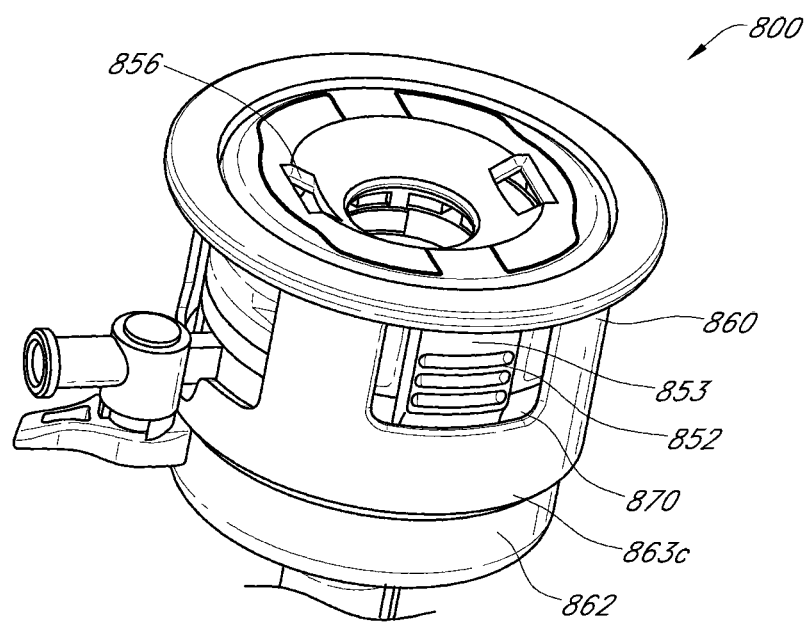
FIG. 42 illustrates a perspective view of a trocar assembly.
Figure 43:
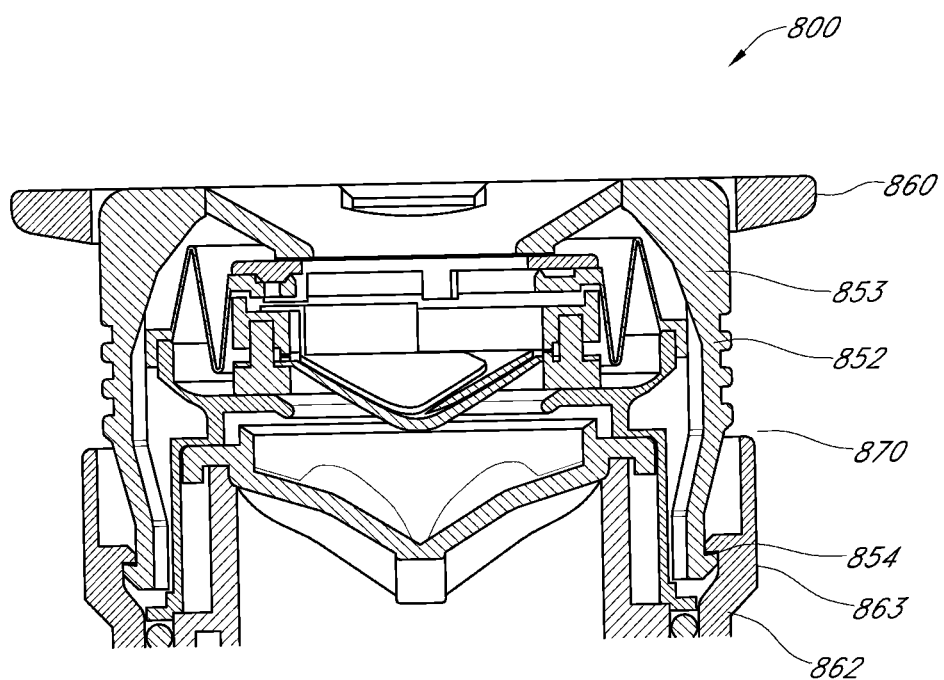
FIG. 43 is a cross sectional view of the trocar assembly of FIG. 42.

FIG. 42 illustrates a perspective view of a trocar assembly 800. FIG. 43 is a cross sectional view of the trocar assembly 800 of FIG. 42. The trocar assembly of FIGS. 42 and 43 can include features that are similar to the features of the trocar assembly 200. Similar features of the trocar assembly 800 will be referred to with similar reference numerals. As described herein, a latching mechanism 852 of the seal cartridge 840 can allow the seal cartridge 840 to be coupled or released from the cannula 860. In some embodiments, the latching mechanism 852 can releasably engage with other portions of the trocar assembly 800. In the illustrated embodiment, the latching mechanism 852 can extend from the body of the seal cartridge 840 into the latching windows 870 defined in the cannula 860 to couple the seal cartridge 840 with the cannula 860. In some embodiments, the latching mechanism 852 includes a latching hook 854 extending from the latching mechanism 852. The latching hook 854 can engage with features of the funnel 862, such as the transition portion 863c to engage the cannula 860.

The latching mechanism 852 can further include an extension portion 853. The extension portion 853 can engage with features of the funnel 862. In the depicted example, the extension portion 853 is movable between an extended or engaged position and a retracted or disengaged position.

Figure 44:
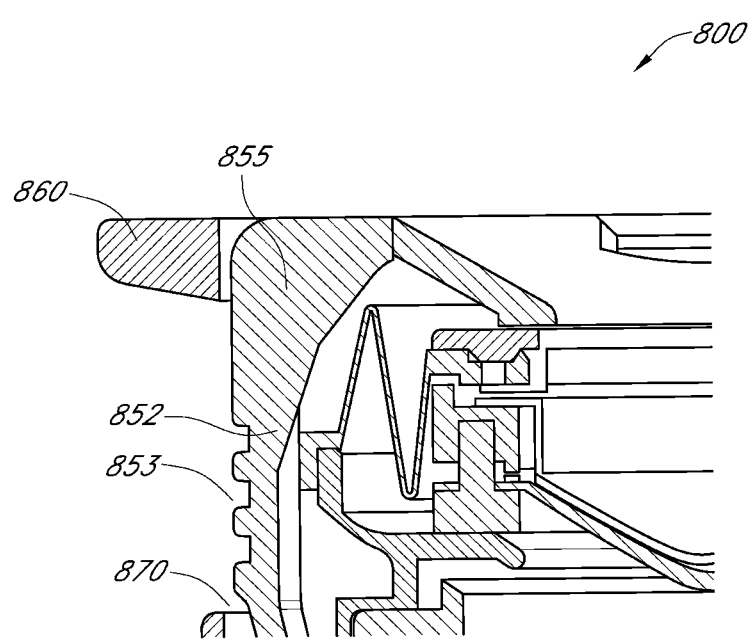
FIG. 44 is a detail cross sectional view of the trocar assembly of FIG. 42 with the latch mechanism in a free state.
Figure 45:
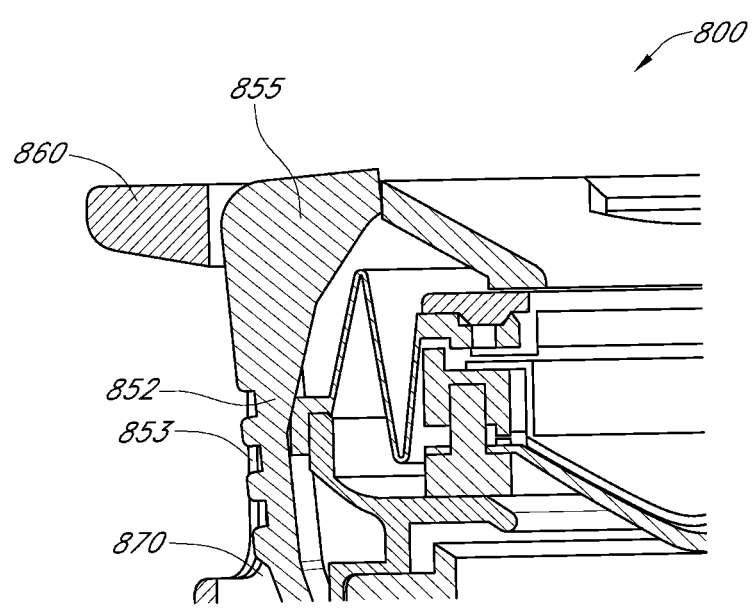
FIG. 45 is a detail cross sectional view of the trocar assembly of FIG. 42 with the latch mechanism in a depressed state.

FIG. 44 is a detail cross sectional view of the trocar assembly 800 of FIG. 42 with the latch mechanism 852 in a free state. FIG. 45 is a detail cross sectional view of the trocar assembly 800 of FIG. 42 with the latch mechanism 852 in a depressed state. In the free or extended position, the extension portion 853 can extend through the latching windows 870 of the cannula 860. In some embodiments, the latching mechanism 852 includes a biasing member to bias the latching mechanism 852 outward to extend and engage with the cannula 860. Optionally, the biasing member can be integral to the latching mechanism.

In the retracted or depressed position, the extension portion 853 can be retracted or spaced apart relative to the latching windows 870 of the cannula 860. As can be appreciated, a clinician can depress the extension portions 853 to disengage the latching mechanism 852 from the cannula 860 to remove the seal cartridge 840. Optionally, the extension portion 853 can include a ridged or grooved portion to allow a clinician to engage the latching mechanism 852.

As illustrated, during actuation, the extension portions 853 of the latching mechanism 852 can be constrained to rotate or pivot between the extended and retracted positions. In some embodiments, the extension portions 853 can rotate inward or upward from the extended position to the retracted position. As illustrated, an upper portion 855 of the extension portions 853 can rotate upward as the extension portions 853 move from the extended position to the retracted position.

Similar to other embodiments, tools such as the obturator can be disposed on a top or proximal surface of the seal cartridge 840. In the illustrated embodiment, the seal cartridge 840 can include one or more latching slots 856 to allow the obturator to couple with the seal cartridge 840. In some embodiments, the latching mechanism of an obturator can extend into the latching slots 856 to couple the obturator or other tools with the seal cartridge 840.

Advantageously, the seal cartridge 840 is configured to prevent the inadvertent removal of the seal cartridge 840 during the removal of the obturator or other tools, preventing inadvertent loss of insufflation. In the depicted example, when the obturator or another tool is coupled to the seal cartridge 840, the latching mechanism 852 of the seal cartridge 840 can prevent the seal cartridge 840 from being removed from the cannula 860. Therefore, the seal cartridge 840 cannot be inadvertently removed from the cannula 860 prior to the removal of the obturator from the cannula 860.

In the depicted example, the seal cartridge 860 can prevent the latching mechanism 852 from being depressed or otherwise actuated prior to the removal of the obturator or other tools from the seal cartridge 840. As illustrated, when the obturator is coupled to the seal cartridge 840, the inner surface of the obturator prevents the extension portions 853 of the latching mechanism 852 from rotating upward, blocking the extension portions 853 from moving to a retracted position and preventing the latching mechanism 852 from releasing the seal cartridge 840.

As can be appreciated, upon disengaging the obturator from the seal cartridge 840, a clinician can depress the extension portions 853 to disengage the latching mechanism 852 from the cannula 860 to remove the seal cartridge 840.

3. Implementing Systems and Terminology

Implementations disclosed herein provide systems, methods and apparatus for operatively coupling an obturator and a cannula.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present inventions. Various modifications to these implementations will be readily apparent to those skilled in the art, and the generic principles defined herein may be applied to other implementations without departing from the scope of the inventions. For example, it will be appreciated that one of ordinary skill in the art will be able to employ a of number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present inventions are not intended to be limited to the implementations shown herein but is to be accorded the widest scope consistent with the principles and novel features disclosed herein.

What is claimed is:

1. A method of operating a surgical device, the method comprising:
   disengaging an obturator from a latching window defined in a funnel portion of a cannula;
   removing a shaft portion of the obturator from a cannula lumen of the cannula;

disengaging a seal cartridge from the funnel portion of the cannula by actuating a release button of the seal cartridge through the latching window; and removing the seal cartridge from the funnel portion after the removing of the shaft portion of the obturator from the cannula lumen, wherein the obturator comprises a release button that circumferentially aligns with the release button of the seal cartridge.

2. The method of claim 1, further comprising:

inserting the shaft portion of the obturator into the cannula lumen of the cannula; and engaging the latching window defined in the funnel portion of the cannula with an obturator latching member of the obturator.

3. The method of claim 1, further comprising engaging an obturator latching member against a brim of the cannula.

4. The method of claim 1, further comprising providing positive pressure within the cannula lumen via a gas port.

5. The method of claim 1, further comprising maintaining positive pressure within the cannula lumen via a sealing portion of the seal cartridge.

6. The method of claim 1, further comprising preventing the removing of the seal cartridge before the disengaging of the obturator.

7. A method of operating a surgical device, comprising:

positioning a seal cartridge within a funnel portion of a cannula;

engaging the seal cartridge with the funnel portion of the cannula;

inserting a shaft portion of an obturator within a lumen of the cannula; and engaging the obturator with the funnel portion of the cannula, wherein the engaging of the obturator with the funnel portion of the cannula includes extending a latching mechanism of the obturator through both the seal cartridge and the cannula, wherein the obturator comprises a release button that circumferentially aligns with a release button of the seal cartridge.

8. The method of claim 7, wherein the inserting of the shaft portion of the obturator within the lumen of the cannula includes extending the shaft portion of the obturator through an orifice of the seal cartridge.

9. The method of claim 7, wherein the engaging of the seal cartridge with the funnel portion of the cannula includes latching the seal cartridge directly to the cannula to form a seal with the cannula.

10. The method of claim 7, further comprising positioning the release button of the seal cartridge with respect to a window of the cannula such that the release button of the seal cartridge is accessible through the window.

11. The method of claim 7, wherein the engaging of the obturator with the funnel portion of the cannula comprises latching the obturator to a brim of the cannula.

12. The method of claim 7, wherein the latching mechanism of the obturator includes the release button of the obturator, and further comprising actuating the release button of the obturator to disengage the obturator from the seal cartridge and the cannula.

13. A method of operating a surgical device, comprising:

positioning a seal cartridge within a funnel portion of a cannula;

engaging the seal cartridge with the funnel portion of the cannula by extending a release button of the seal cartridge through a window in a sidewall of the cannula;

inserting a shaft portion of an obturator within a lumen of the cannula; and latching the obturator directly to the cannula through the window.

14. The method of claim 13, wherein the seal cartridge is configured to latch directly to the cannula.

15. The method of claim 14, wherein the obturator is configured to latch directly to a brim of the cannula.

16. The method of claim 13, wherein the obturator comprises a release button that circumferentially aligns with the release button of the seal cartridge.

17. The method of claim 13, wherein the cannula comprises another window that is approximately 180 degrees apart from the window.

18. The method of claim 13, wherein a latching mechanism of the obturator extends through the release button of the seal cartridge to couple to a brim of the cannula.

19. The method of claim 13, wherein a top segment of the obturator has a diameter greater than a diameter of a lower portion of the funnel portion of the cannula.

* * * * *